US010376476B2

(12) United States Patent
Mus-Veteau et al.

(10) Patent No.: US 10,376,476 B2
(45) Date of Patent: Aug. 13, 2019

(54) PANICEIN COMPOUNDS, COMPOSITIONS AND USES THEREOF

(71) Applicants: CENTRE NATIONAL DE LA RECHERCHE SCIENTIFIQUE, Paris (FR); UNIVERSITE NICE SOPHIA ANTIPOLIS, Nice (FR)

(72) Inventors: Isabelle Mus-Veteau, Valbonne (FR); Olivier Thomas, Galway (IE); Marie-Aude Tribalat, Les Arcs (FR); Stephane Azoulay, Nice (FR)

(73) Assignees: UNIVERSITE NICE SOPHIA ANTIPOLIS, Nice (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 0 days.

(21) Appl. No.: 15/920,486

(22) Filed: Mar. 14, 2018

(65) Prior Publication Data
US 2018/0200200 A1    Jul. 19, 2018

Related U.S. Application Data

(62) Division of application No. 15/522,300, filed as application No. PCT/EP2015/074771 on Oct. 26, 2015, now abandoned.

(30) Foreign Application Priority Data

Oct. 27, 2014  (EP) .................................. 14306710

(51) Int. Cl.
*A61K 31/05* (2006.01)
*A61K 31/11* (2006.01)
*A61K 31/353* (2006.01)

(52) U.S. Cl.
CPC .............. *A61K 31/05* (2013.01); *A61K 31/11* (2013.01); *A61K 31/353* (2013.01)

(58) Field of Classification Search
CPC ..................................................... A61K 31/05
USPC ....................................................... 514/731
See application file for complete search history.

(56) References Cited

U.S. PATENT DOCUMENTS

2013/0012591 A1* 1/2013 Butler ................. A61K 31/167
                                                      514/613
2014/0011277 A1   1/2014 Mus-Veteau et al.

FOREIGN PATENT DOCUMENTS

WO    WO 2012/080630    6/2012

OTHER PUBLICATIONS

Wang, J. et al,. (Molecular Cancer Therapeutics vol. 13 pp. 16-26. Published online Nov. 18, 2013) (Year: 2013).*

Zubia et al (Tetrahedron vol. 50 pp. 8153-8160 published 1994) (Year: 1994).*
Stedman Medical Dictionary 27th edition published 2000 (Year: 2000).*
Casapullo et al (J. Nat Prod. vol. 56 pp. 527-533 Published 1993) (Year: 1993).*
Cretnik et al (International Journal of Oncology Vo. 34 pp. 1040-1050 published 2009) (Year: 2009).*
Zubia, E., et al., Tetrahedron vol. 50 pp. 8153-8160. Published 1994. (Year: 1994).*
Casapullo, A. et al., J. of Natural Products vol. 56 pp. 527-533. Published 1993. (Year: 1993).*
Singh, S., et al., Cancer Research vol. 71 pp. 4453-4463. Published 2011 (Year: 2011).*
Bar, E. E. et al. "Hedgehog Signaling Promotes Medulloblastoma Survival via Bc/II" *The American Journal of Pathology*, Jan. 1, 2007, pp. 347-355, vol. 170, No. 1.
Casapullo, A. et al. "Paniceins and Related Sesquiterpenoids from the Mediterranean Sponge *Reniera fulva*" *Journal of Natural Products*, Apr. 1993, pp. 527-533, vol. 56, No. 4.
Zubia, E. et al. "Sesquiterpene Hydroquinones from the Sponge *Reniera mucosa*" *Tetrahedron*, Jan. 1, 1994, pp. 8153-8160, vol. 50, No. 27.
Written Opinion in International Application No. PCT/EP2015/074771, dated Feb. 1, 2016, pp. 1-6.
Monks, A. et al. "Feasibility of a High-Flux Anticancer Drug Screen Using a Diverse Panel of Cultured Human Tumor Cell Lines" *Journal of the National Cancer Institute*, Jun. 5, 1991, pp. 757-766, vol. 83, No. 11.

(Continued)

*Primary Examiner* — Timothy P Thomas
*Assistant Examiner* — George W Kosturko
(74) *Attorney, Agent, or Firm* — Saliwanchik, Lloyd & Eisenschenk

(57) ABSTRACT

The present invention relates to the fields of medicine and cancer treatment. The invention more specifically relates to the use of a panicein or a derivative thereof, to decrease or inhibit, in vitro or ex vivo, the Patched receptor drug efflux activity, in particular the chemotherapeutic drug efflux activity and chemotherapy resistance.

Figure 1:
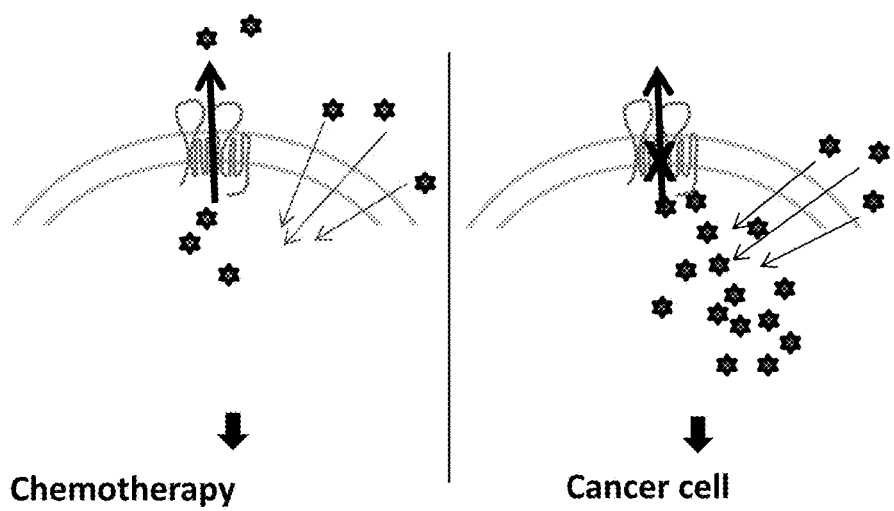

The present disclosure further relates to uses of such compounds, in particular to prepare a pharmaceutical composition to allow or improve the efficiency of a therapy of cancer in a subject in need thereof. The compound of the invention can indeed be advantageously used, in combination with at least one chemotherapeutic drug, for treating cancer, for preventing cancer metastasis and/or for preventing cancer recurrence in a subject.

The invention also discloses methods for preventing or treating cancer, cancer metastasis and/or cancer recurrence in a subject, as well as kits suitable for preparing a composition according to the present invention and/or for implementing the herein described methods.

14 Claims, 17 Drawing Sheets
(5 of 17 Drawing Sheet(s) Filed in Color)

(56) References Cited

OTHER PUBLICATIONS

Christgen, M. et al. "MDA-MB-435: The questionable use of a melanoma cell line as a model for human breast cancer is ongoing" *Cancer Biology & Therapy*, Sep. 2007, pp. 1355-1357, vol. 6, No. 9.
PCT International Search and Preliminary Examination Guidelines. World Intellectual Property Organization. Published Mar. 11, 2004, pp. 1-205.

\* cited by examiner

P2:
Panicein C

P3:
Panicein B3

P4:
Panicein B2

P5:
Panicein A hydroquinone

A

B

C

D

B

PANICEIN COMPOUNDS, COMPOSITIONS AND USES THEREOF

CROSS-REFERENCE TO RELATED APPLICATIONS

This application is a divisional of U.S. application Ser. No. 15/522,300, filed Apr. 27, 2017, which is the U.S. national stage application of International Patent Application No. PCT/EP2015/074771, filed Oct. 26, 2015.

FIELD OF THE INVENTION

The present disclosure generally relates to the fields of medicine and cancer treatment.

The invention more specifically relates to the use of a panicein or a derivative or analogue thereof, to decrease or inhibit, in vitro or ex vivo, the Patched receptor drug efflux activity, in particular the chemotherapeutic drug efflux activity and chemotherapy resistance.

The present disclosure further relates to uses of such compounds, in particular to prepare a pharmaceutical composition to allow or improve the efficiency of a cancer therapy in a subject in need thereof. The compounds of the invention can indeed be advantageously used, in combination with at least one chemotherapeutic drug, for treating cancer, for preventing cancer metastasis and/or for preventing cancer recurrence in a subject.

The invention also discloses methods for preventing or treating cancer, cancer metastasis and/or cancer recurrence in a subject. The present invention in addition provides kits suitable for preparing a composition according to the present invention and/or for implementing the herein described methods.

BACKGROUND OF THE INVENTION

Eight million people die each year from cancer worldwide. Cancer is the second cause of death in the United States and in Europe. For many solid tumors, in spite of the reduction of the carcinoma by surgery and first-line chemotherapy, resistance to the drugs causing the death of patients is developed. This phenomenon of resistance to chemotherapeutic agents is a real public health problem.

The Hedgehog (Hh) signaling pathway controls cell differentiation and proliferation. It plays a crucial role during embryonic development and, in adulthood, in stem cell homeostasis and tissue regeneration. However, Hh signaling is also involved in cancer development, progression, and metastasis. Indeed, aberrant activation of the Hh signaling has been identified in many aggressive cancers such as breast cancer, lung cancer, colorectal cancer, ovarian cancer, pancreatic cancer, melanoma or multiple myeloma (Varjosalo and Taipale 2008; Scales and de Sauvage, 2009), in particular in cells exhibiting resistance to chemotherapeutic agents such as cancer stem cells or tumor initiating cells. Recently, Yue et al. (2014) showed that Hh signaling is involved in lung squamous cell carcinomas (SCC) recurrence, metastasis and resistance to chemotherapy. Several studies have shown that antagonizing the Hh signaling receptor Smoothened (Smo) could provide a way to interfere with tumorigenesis and tumor progression. The most commonly used antagonist of the Hh pathway is the plant alkaloid cyclopamine (Taipale et al. 2000). Genentech has a long lasting research project on Hh pathway and has identified a new drug for basal-cell carcinoma treatment. Vismodegib is a first-in-class investigational, oral medicine that is designed to selectively inhibit Hh signaling by targeting Smo (Garber, 2008 Scales and de Sauvage, 2009). It has been reported that autocrine expression of Hh morphogenes such as Sonic Hedgehog (Shh) is required for growth of some cancers (Dahmane et al., 1997; Karhadkar et al., 2004), and stromal cell-derived Shh can also activate the Hh pathway in tumors (Becher et al., 2008). One Shh-specific monoclonal antibody (5E1) has been shown to block the growth of some tumors, including small-cell lung carcinoma (Watkins et al., 2003). In addition to targeting tumors that have hyperactive Hh pathway themselves, antagonists of the Hh pathway could also affect growth of tumors that use Hh ligands to induce angiogenesis (Pola et al., 2001; Nagase et al., 2008) or recruit other types of stromal cells supporting tumor growth. Because adults can tolerate inhibition of the Hh pathway (Berman et al., 2002; Kimura et al., 2008), specifically blocking Hh signaling offers an effective treatment for the various cancers originating from aberrant Hh pathway activation. However, systemic treatment of pediatric tumors such as medulloblastoma may not be feasible due to the severe effects that transient inhibition of the Hh pathway has on bone growth (Kimura et al., 2008).

Two different genes (Patched 1 and Patched 2) encode homologues of Drosophila Patched, the Hh morphogen receptor. Mice deficient in Patched 2 are viable, but develop alopecia and epidermal hypoplasia and have increased tumor incidence in the presence of one mutant allele of Patched 1. Loss of Patched 1, in turn, results in complete activation of the Hh pathway, suggesting that Patched 1 is the functional ortholog of Drosophila Patched (Varjosalo and Taipale, 2008). Patched 1, referred to as Patched, whose expression is induced upon activation of the Hh pathway, is overexpressed in many cancers: lung, breast, basal cells of the skin, prostate, colon, brain (Scales and de Sauvage, 2009; Blotta et al., 2012; Jeng et al., 2014) and myeloid leukemia (Zhao et al., 2009; Queiroz et al., 2010). Recent studies suggest Patched as an early marker of gastric and thyroid cancers (Saze Z et al., 2012; Xu X et al., 2012). As already described, in some cancers, the morphogen Hh is overproduced by cancer cells themselves and activates Hh signaling by interacting with its receptor Patched. Nakamura and co-workers showed in 2007 that the use of an antibody directed against one of the extracellular domains of Patched involved in the interaction with Hh inhibits proliferation of pancreatic cancer cells. In 2012, they showed that three peptides from Hh involved in interaction with Patched could suppress the proliferation of two pancreatic cancer cell lines and decrease the expression of the transcription factor Gli1 both in vitro and in vivo (Nakamura et al., 2012).

Inventors discovered that the Hh receptor Patched has a drug efflux activity and can contribute to the resistance of cancer cells to chemotherapeutic agents (Bidet et al., 2012; patent WO2012/080630). Indeed, they have shown that the human Patched protein expressed in yeast confers resistance to various chemotherapeutic agents used to treat many metastatic cancers (doxorubicin, methotrexate, temozolomide, 5-FU) and effluxes doxorubicin. This yeast model has been extended to fibroblasts (often used for the study of the Hh pathway) and human cancer cell lines overexpressing Patched such as melanoma and Leukemia cell lines. These cells release (efflux) less doxorubicin in the presence of the Patched ligand Hh, which induces Patched internalization and degradation. Viability tests carried out with these different cell lines showed that the presence of Hh increases the cytotoxicity of doxorubicin. These results suggest that the Hh receptor Patched can participate in the phenomenon of resistance to chemotherapeutic agents of cancer cells and allowed to propose Patched as a new target for anti-cancer therapy (patent WO2012/080630) (FIG. 1).

Currently, no antagonist of Patched is available. There is thus a need for compounds able to inhibit the drugs efflux activity of the Patched receptor and which may be used in cancer therapy.

SUMMARY OF THE INVENTION

Inventors now provide active molecules for preventing drug efflux from cancer cells, in particular chemotherapeutic agent efflux. These molecules allow the physician to prevent or control, preferably decrease, cancer cell proliferation by inhibiting Patched drug efflux activity. They are advantageously capable of increasing the effectiveness of chemotherapeutic treatments directed against any cancer which expresses Patched. Inventors herein demonstrate that these molecules are in addition capable of reducing the risk of metastasis and/or cancer recurrence.

The present invention thus relates to the use of a panicein compound, or of a derivative or analogue thereof, to decrease or inhibit, in vitro or ex vivo, the Patched receptor drug efflux activity.

In a particular embodiment, the panicein compound is a compound of formula (I)

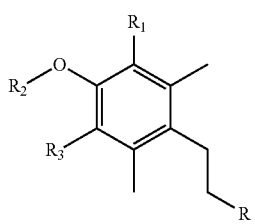

(I)

wherein:
$R_1$ represents H, $C_1$-$C_6$ alkyl, $C_1$-$C_6$ aminoalkyl, $C_1$-$C_6$ hydroxyalkyl, $C_1$-$C_6$ halogenoalkyl or —$OR_4$,
$R_2$ is H or $C_1$-$C_6$ alkyl,
$R_3$ represents $C_1$-$C_6$ alkyl, —$CH_2OR_4$, —$C(=O)R_4$, —$C(=O)OR_4$, —$C(=O)NHR_4$, or —$CH_2NHR_4$
each $R_4$ is independently —H, or a $C_1$-$C_6$ alkyl.
R is selected from the group consisting of:

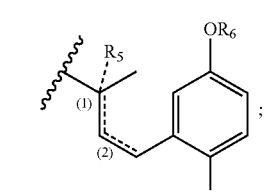

(IIa)

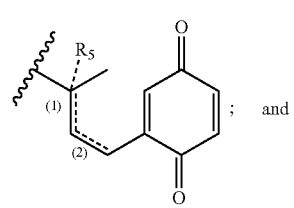

(IIb) ; and

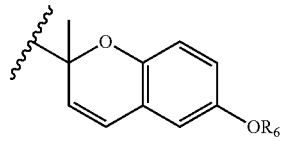

(IIc)

wherein:
bonds (1) and (2) are independently of each other a single bound or a double bond, preferably bonds (1) and (2) are not simultaneously double bonds,
$R_5$ is present when bond (1) is a single bond. When present $R_5$ represents —H, or —$OR_6$, and
When present, each $R_6$ is independently H or a $C_1$-$C_6$ alkyl or a pharmaceutically acceptable salt thereof.

In a particularly preferred embodiment, the compound of formula (I) is selected from Panicein C, Panicein B3, Panicein B2 and Panicein A hydroquinone.

Also herein described is a panicein compound for use, in combination with at least one chemotherapeutic drug, for treating cancer, for preventing cancer metastasis and/or for preventing cancer recurrence in a subject.

Another object of the invention is a composition comprising at least one panicein compound and preferably at least one chemotherapeutic drug to be used simultaneously, separately or sequentially, typically for use for treating cancer, for preventing cancer metastasis and/or for preventing cancer recurrence in a subject.

Also herein described is a kit comprising at least one panicein compound and at least one chemotherapeutic drug in distinct containers, as well as uses of said kit typically to prepare a composition according to the present invention.

DETAILED DESCRIPTION OF THE INVENTION

Inventors demonstrated that the Patched receptor is involved in the efflux of drugs such as doxorubicin, a chemotherapeutic agent used for clinical management of recurrent cancers, suggesting that Patched could contribute to chemotherapy resistance of cancer cells (Bidet et al. 2012, WO2012/080630). They developed innovative tests to identify molecules able to inhibit Patched drug efflux activity. The first test was based on the ability of molecules to inhibit growth of yeast over-expressing human Patched on medium containing doxorubicin. Active molecules were then tested for their ability to increase 1) doxorubicin cytotoxicity on cancer cell lines over-expressing Patched, 2) the cytotoxic effect of doxorubicin on several melanoma cell lines, and 3) the chemotherapeutic drugs cytotoxicity on different cancer cell lines expressing Patched. The molecules are also tested for tumor treatment and prevention of metastasis development on mice grafted with human melanoma cells as well as on a mice model of breast cancer recurrence and metastasis.

In this context, the Inventors demonstrated that certain compounds extracted from marine sponges, in particular paniceins, were able to inhibit the efflux of chemotherapeutic agents such as doxorubicin, dacarbazine and cisplatine in patched-overexpressing yeasts, whereby the growth of the yeast was inhibited. The Inventors further showed that panicein compounds of the invention significantly increased the sensitivity of patched-expressing melanoma cell lines to doxorubicin. As fully-shown in the below examples, the cytotoxicity of doxorubicin on patched-expressing melanoma cell lines was significantly increased when doxorubicin was used in combination with a panicein such as Panicein C, Panicein B3, Panicein B2 or Panicein A hydroquinone.

Noteworthy, the tested paniceins did not show any significant cytotoxicity towards melanoma cells, when used alone (i.e. in the absence of any chemotherapeutic agent), at concentrations up to 20 µM.

To the knowledge of the Inventors, the ability of paniceins to inhibit Patched receptor and to potentiate the cytotoxicity of chemotherapeutic agents such as doxorubicin towards Patched receptor-expressing cancer cells was neither described nor suggested in the prior art.

A first object of the invention thus concerns the use of a panicein compound, or derivatives and analogues thereof, to decrease or inhibit, in vitro or ex vivo, the Patched receptor drug efflux activity.

As used herein, panicein compounds (also called herein "paniceins") refer to sesquiterpenoid quinones and corresponding quinols. Paniceins are, in particular, extracted from marine organisms such as marine sponges, in particular Mediterranean marine sponges. For instance, the paniceins such as Panicein C, Panicein B3, Panicein B2 and Panicein A hydroquinone can be isolated from Mediterranean marine sponges belonging to *Haliclona* genus such as *Haliclona mucosa*. Another marine sponge of interest for the isolation of paniceins is, for example, *Halichondria panacea*. Methods for extracting paniceins and related compounds from marine sponges are described, among others, in Casapullo et al. (1973), the disclosure of which being incorporated herein by reference.

As used herein, an analogue or a derivative encompasses compounds having a chemical structure derived from a sesquiterpenoid quinone or a sesquiterpenoid quinol. In a particular embodiment, an analogue or a derivative of a panicein may refer to a stereoisomer of a naturally-occurring panicein or may refer to a compound which differs from a naturally-occurring panicein in virtue of one or several chemical modifications. Chemical modifications include, without being limited to, the introduction of a chemical substituent or the replacement of a chemical group by another, in particular by a bioisostere group (i.e. with similar physical or chemical properties) or by a chemical group enhancing or improving the properties of the panicein, such as the biological activity, the solubility, the pharmacokinetic properties or the cell-targeting. As used herein, analogues and derivatives encompass, without being limited to, stereoisomers, prodrugs and metabolites of paniceins.

In a more specific embodiment, the invention relates to the use of a compound of formula (I):

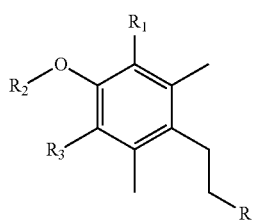

wherein:
$R_1$ is H, $C_1$-$C_6$ alkyl, $C_1$-$C_6$ aminoalkyl, $C_1$-$C_6$ hydroxyalkyl, $C_1$-$C_6$ halogenoalkyl or —$OR_4$,
$R_2$ is H or $C_1$-$C_6$ alkyl, $R_3$ is $C_1$-$C_6$ alkyl, —$CH_2OR_4$, —C(=O)$R_4$, —C(=O)$OR_4$, —C(=O)$NHR_4$, or —$CH_2NHR_4$
each $R_4$ is independently —H, or $C_1$-$C_6$ alkyl.
R is selected from the group consisting of:
a radical of formula (IIa):

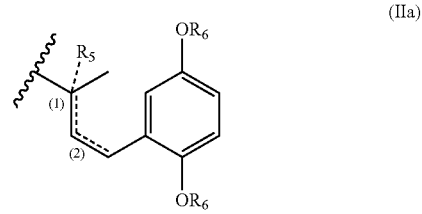

a radical of formula (IIb):

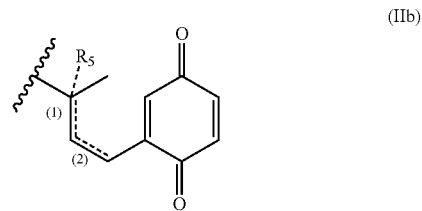

and
a radical of formula (IIc):

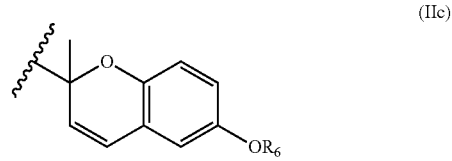

wherein:
bonds (1) and (2) are independently of each other a single bond or a double bond, preferably bonds (1) and (2) are not simultaneously double bonds,
$R_5$ is present when bond (1) is a single bond. When present, $R_5$ represents —H, or —$OR_6$. Preferably, when present, $R_5$ is H or OH, and
when present, each $R_6$ is independently H or a $C_1$-$C_6$ alkyl, preferably each $R_6$ is H or a $C_1$-$C_3$ alkyl such as $CH_3$,
or a pharmaceutically acceptable salt thereof, to decrease or inhibit, in vitro or ex vivo the Patched receptor drug efflux activity.

It goes without saying that when bond (1) is a double bond, $R_5$ is absent.

As used herein, the term "pharmaceutically acceptable" refers to compositions, compounds, salts and the like that are, within the scope of sound medical judgment, suitable for contact with the tissues of the subject, or which can be administered to the subject, without excessive toxicity or other complications commensurate with a reasonable benefit/risk ratio. For instance, pharmaceutically acceptable salts encompass sodium, potassium, chloride, ammonium, acetate salts and the like.

As used herein, a $C_1$-$C_6$ alkyl encompasses linear or branched alkyl radicals comprising from 1 to 6 carbon atoms. Preferred $C_1$-$C_6$ alkyl groups are $C_1$-$C_3$ alkyl such as methyl, ethyl, propyl and isopropyl. A particularly preferred alkyl group is methyl.

A "hydroxyalkyl" refers to a radical of formula -A-OH wherein A represents an alkylene group.

A "aminoalkyl" refers to a radical of formula -A-NH$_2$ wherein A represents an alkylene group.

A "halogenoalkyl" refers to a radical of formula -A-Hal wherein A represents an alkylene group and Hal represents a halogen such as Cl, Br, I, or F.

As used herein, "hydroxyalkyl", "aminoalkyl" and "halogenoalkyl" comprise from 1 to 6 carbon atoms, preferably from 1 to 3 carbon atoms.

In a particular embodiment, bond (1) is a single bond and bond (2) is a double bond. In another embodiment, bond (1) is a double bond and bond (2) is a single one.

In some embodiments, the compound of formula (I) comprises one or several of the following features:

i. $R_1$ is H, $C_1$-$C_6$ alkyl, or —$OR_4$, and/or
ii. $R_2$ is H or $C_1$-$C_6$ alkyl, and/or
iii. $R_3$ is $C_1$-$C_6$ alkyl, —$CH_2OR_4$ or, —$C(=O)R_4$, and/or
iv. each $R_4$ is independently —H, or a $C_1$-$C_6$ alkyl, preferably a $C_1$-$C_3$ alkyl.

In a particular embodiment, the compound of the invention comprises all the above listed features.

In some other embodiments, the compound of formula (I) comprises one or several (1, 2 or 3) of the following features:

(i) $R_1$ is H, or OH, and/or
(ii) $R_2$ is H or $CH_3$, and/or
(iii) $R_3$ is —$CH_3$ or —$C(=O)H$.

In some alternate or additional embodiments, the compound of formula (I) is such that R is selected from the group consisting of:

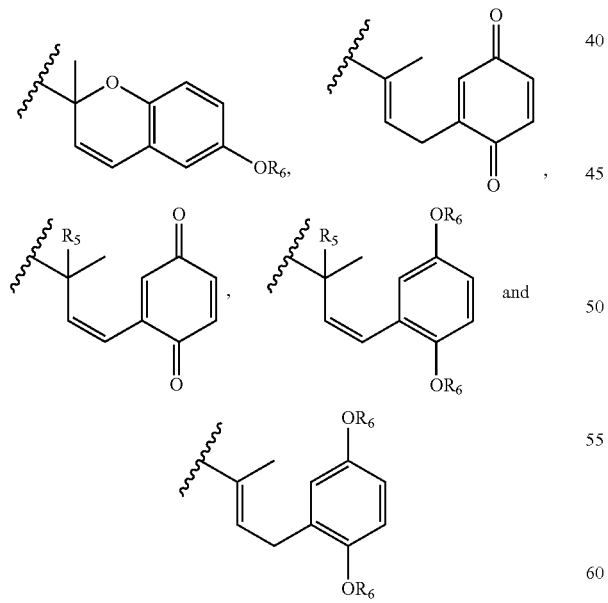

wherein $R_6$ and $R_5$ are as defined above. Preferably, $R_5$ is H or OH. Preferably, each $R_6$ is H.

In some other embodiments, the compound of formula (I) is such that R is selected from the group consisting of:

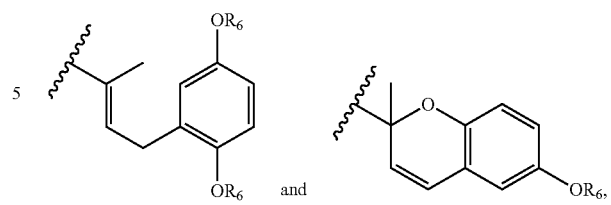

$R_6$ being as defined above.

In a particular aspect, the compound of formula (I) may be such that R is

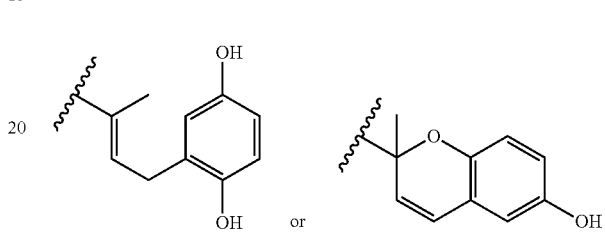

In some particular embodiments, the compound of formula (I) is a naturally-occurring panicein, which means that said compound is obtainable from an organism, in particular from a marine sponge, e.g. by extraction. Preferably, the compound of formula (I) is selected from paniceins as shown in table (I) hereunder, pharmaceutically acceptable salts, metabolites and prodrug thereof as well as stereoisomers thereof.

TABLE I

Examples of panicein compounds according to the invention

Panicein A

Panicein B

TABLE I-continued

Examples of panicein compounds according to the invention

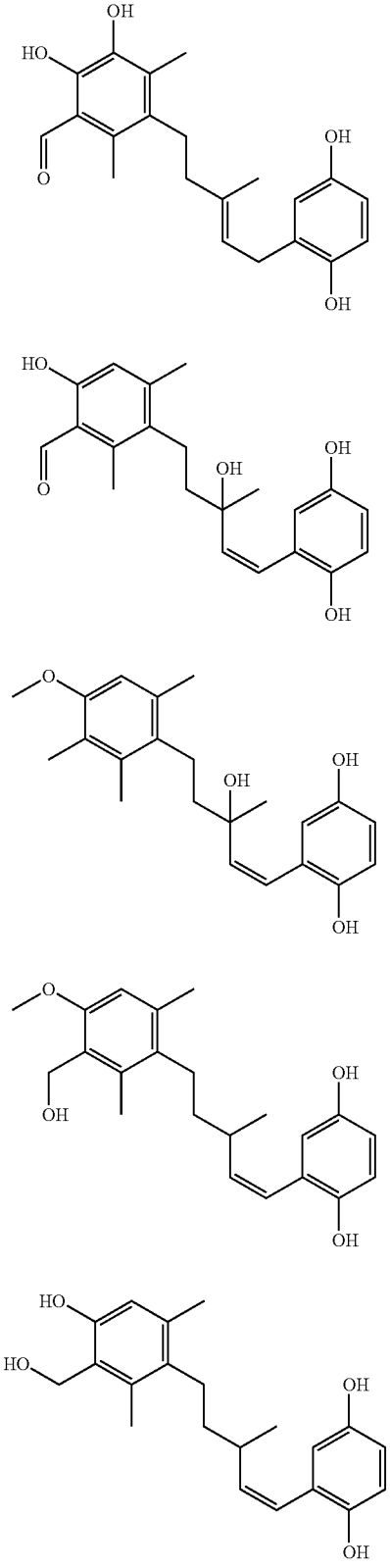

Panicein C

Panicein D

Panicein E

Panicein F1

Panicein G

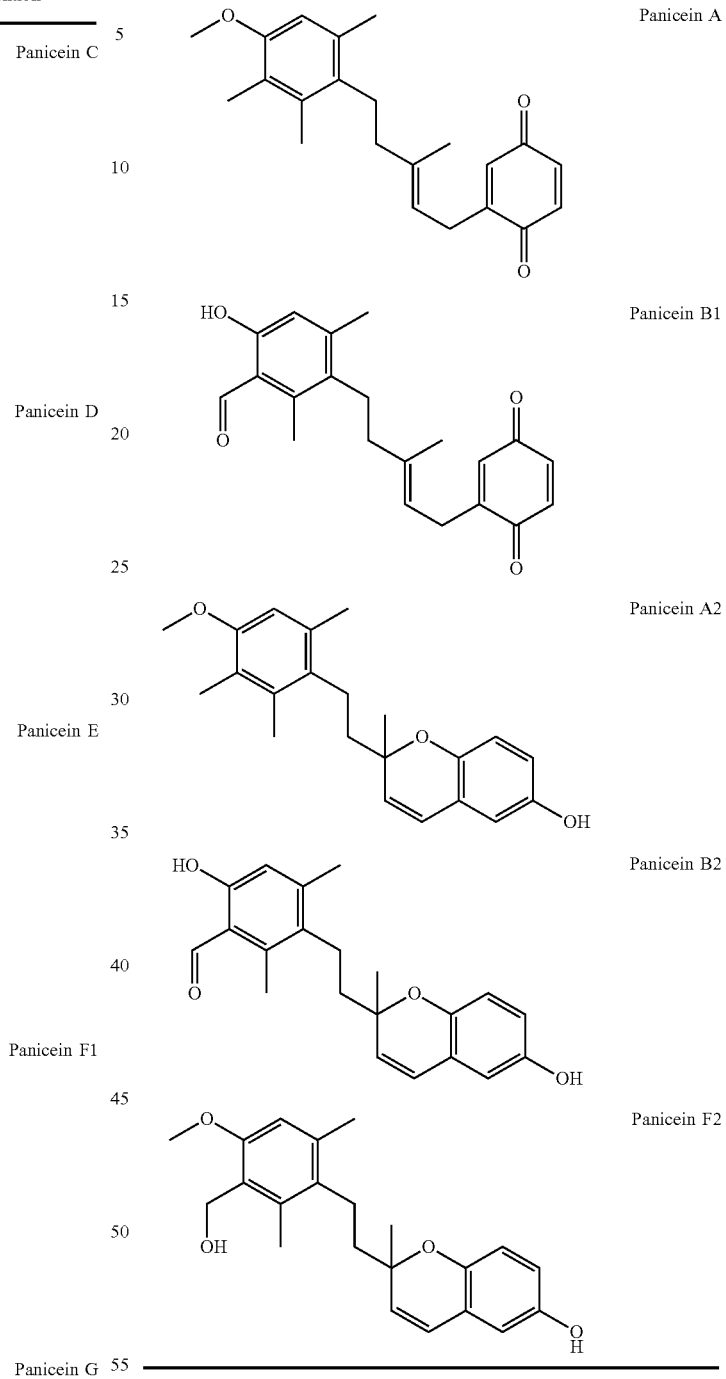

Panicein A

Panicein B1

Panicein A2

Panicein B2

Panicein F2

In some embodiments, the compound of formula (I) is selected among Panicein A hydroquinone, Panicein B3, Panicein C, Panicein G, Panicein A, Panicein B1, Panicein B2 and Panicein C.

In some particular embodiments, the compound of formula (I) is distinct from Panicein D, Panicein E, Panicein F1 and Panicein A2.

In some preferred embodiments of the invention, the compound of formula (I) is selected from the group consisting of:

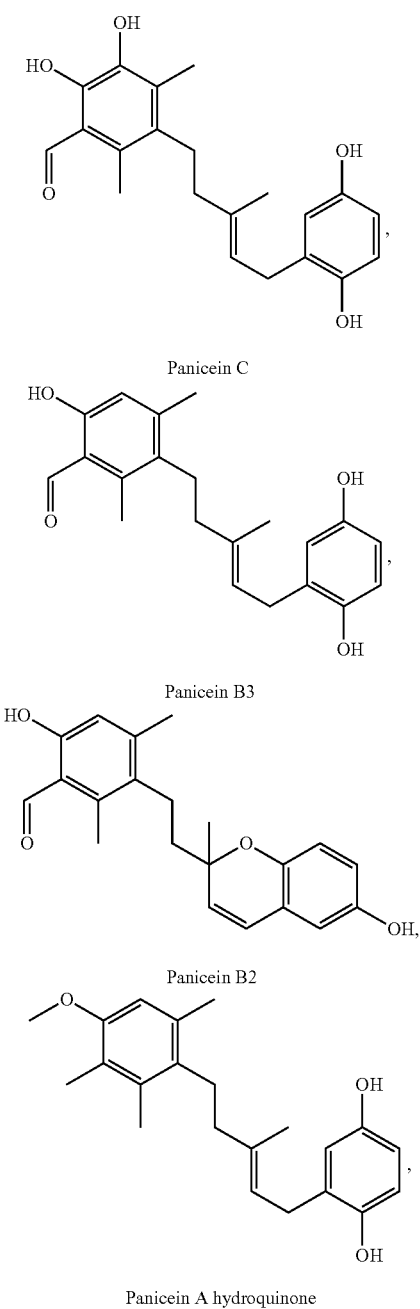

Panicein C

Panicein B3

Panicein B2

Panicein A hydroquinone and pharmaceutically acceptable salt thereof.

In another preferred embodiment of the invention, the compound of formula (I) is a derivative or analog of Panicein A hydroquinone, Panicein C, Panicein B3, and Panicein B2, preferably a derivative or analog of Panicein A hydroquinone.

A preferred derivative or analog of Panicein A hydroquinone is Panicein A quinone.

The compounds of the invention can be obtained by methods well-known by the skilled artisan such as extraction, hemi-synthesis or total synthesis. For instance, methods for extracting paniceins and related compounds from marine sponges are described, among others, in Casapullo et al. (1973) and Zubia et al. (1994), the disclosure of which is incorporated herein by reference. Paniceins may be also prepared by chemical synthesis. For example, Davis et al. (2005) describe the total synthesis of panicein A. Analogues or derivatives of paniceins can be obtained by total synthesis, or by hemi-synthesis from paniceins obtained by extraction, by using conventional chemical reactions.

In a further aspect, the invention relates to the use of an extract comprising at least one panicein compound or derivative thereof for decreasing or inhibiting, in vitro or ex vivo, the Patched receptor drug efflux activity. In some embodiments, said extract may comprise several paniceins. For instance, said extract may comprise 2, 3, 4, 5, 6, or more, distinct paniceins.

Preferred extracts are obtained from a marine sponge, such as *Haliclona mucosa* or *Halichondria panicea*. Other marine sponges of interest for obtaining a panicein or an extract of the invention encompass, without being limited, to *Ircinia variabilis, Agelas oroides, Cymbaxinella damicornis, Aplysina cavemicola, Haliclona fulva, Crambe crambe, Haliclona sarai, Acanthella acuta*, and *Crambe tailliezi*.

A particular extract comprises at least 10 μg/mL of a panicein according to the present invention, or of a mixture of such paniceins. Also encompassed in the present invention is a purified fraction of such an extract. A particular extract is a methanolic extract comprising at least 10 μg/mL final concentration of a panicein, for example 15 or 20 μg/mL.

The invention also relates to the use of at least one compound of formula (I) or a pharmaceutically acceptable salt thereof for increasing the sensitivity of a cancer to a chemotherapeutic agent.

A further object of the invention is the use of at least one compound of formula (I) or a pharmaceutically acceptable salt thereof for decreasing the resistance of a cancer with respect to a chemotherapeutic agent.

Also described is a compound of formula (I) according to the invention (or a pharmaceutically acceptable salt thereof), or a composition comprising at least two compound of formula (I) according to the invention (or pharmaceutically acceptable salts thereof), for use, in combination with at least one chemotherapeutic drug, for treating cancer, for preventing cancer metastasis and/or for preventing cancer recurrence in a subject.

The term "subject" refers to any subject and typically designates a patient, in particular a subject undergoing a treatment of cancer such as chemotherapy and/or radiotherapy, or a subject at risk, or suspected to be at risk, of developing a cancer.

The subject is preferably a mammal, even more preferably a human being, for example a human being suffering from a cancer and resistant to chemotherapy.

The subject is typically a cancer patient, preferably a patient whose tumor cells express the Patched receptor and/or a patient whose stromal and/or tumor cells express the Hedgehog (Hh) protein, and the patient is preferably resistant to chemotherapy.

The subject may have been exposed to part of a complete conventional treatment protocol, for example to at least one cycle of the all treatment protocol, for example two cycles of the all treatment protocol.

The cancer may be any kind of cancer or neoplasia so long as the tumor or cancer cells express or over-express the Patched receptor. A typical cancer is a cancer resistant to the first-line chemotherapy.

The cancer expressing or over-expressing the Patched receptor or having an aberrant expression of the Hh pathway is for example selected from a melanoma (Cretnick et al. 2009), a breast cancer Smith et al. 2014, Jeng K.-S. et al.

2013), a thyroid cancer (Hinterseher al. 2014, Xu H. et al. 2012), a prostate cancer (Kim et al. 2011, Chung et al. 2010), a colon cancer (Wang et al. 2013, Xu M. et al. 2012), a rectal cancer (Qualtrough et al. 2004), an oesophagus cancer (Zhu W. et al. 2011), a gastric cancer (Lee SJ et al. 2013), an ovarian cancer (Sabol et al. 2012), a lung cancer (Li et al. 2012, Gialmanidis et al. 2009), a pancreatic cancer (Ma et al. 2014, Nakamura et al. 2012), a glioma (Yu et al. 2014), an adrenocortical carcinoma (Mus-Veteau et al., unpublished data), pediatric solid malignant tumors such as a neuroblastoma, a rhabdomyosarcoma, a nephroblastoma or a hepatoblastoma (Oue et al. 2010), but also non solid cancers, for example a leukaemia such as a lymphoid leukemia or a myeloid leukemia (Cea et al. 2013), a multiple myeloma (Blotta et al. 2012), and a sarcoma such as an osteosarcoma (Lo et al. 2014). See data from the Protein data bank and Oncomine presented in FIG. 9. This cancer can be a metastatic cancer or not.

In a particular embodiment of the present invention, the chemotherapeutic agent is an agent selected for example from an anthracycline, an antitumor antibiotic, an alkylating agent, an antimetabolite, a plant alkaloid, a topoisomerase inhibitor, an anti-mitotic agent such as a spindle poison, a DNA-intercalating agent, a taxane, an alkylating agent, a platin based component, a specific kinase inhibitor, an hormone, a cytokine, an antiangiogenic agent, an antibody, in particular a monoclonal antibody, and a TLR (Toll-like receptor)-3 ligand.

The treatment which can include several chemotherapeutic agents is selected by the cancerologist depending on the specific cancer to be prevented or treated.

Antitumor antibiotics include for example Bleomycin, Daunorubicin, Doxorubicin, Epirubicin, hydroxyurea, Idarubicin, Mitomycin C or Mitoxantrone.

Alkylating agents include for example dacarbazine, busulfan, Carboplatin, chlorambucil, Cisplatin, Cyclophosphamide, Ifosfamide, Melphalan, the Mechlorethamine, Oxaliplatin, Uramustine or Temozolomide.

Examples of antimetabolites are Azathioprine, Capecitabine, Cytarabine, Floxuridine, Fludarabine, Fluorouracil, Gemcitabine, Methotrexate, Fluorouracil (5-FU) or Pemetrexed; Vegetable alkaloids include for example vinblastine, or vincristine (Vinorelbine); Topoisomerase inhibitors include, for example Irinotecan, Topotecan or Etoposide; Spindle poisons are for example selected from Vinblastine, Vincristine and Vinorelbine.

Taxanes are for example selected from docetaxel, larotaxel, cabazitaxel, paclitaxel (PG-paclitaxel and DHA-paclitaxel), ortataxel, tesetaxel, and taxoprexin.

Examples of platin-based components are CDDP and OXP.

Examples of specific kinase inhibitors are for example BRAF kinase inhibitors such as vemurafenib.

Tamoxifen and antiaromatase drugs are typically used in the context of hormonotherapy.

Examples of cytokines usable in the context of an immunotherapy are IL-2 (Interleukine-2) and IFN (Interferon) alpha (IFNa).

Anti-CD20 (pan B-Cell antigen) or anti-Her2/Neu (Human Epidermal Growth Factor Receptor-2/NEU) are examples of monoclonal antibodies.

In a preferred embodiment, the chemotherapeutic drug or agent is selected from cisplatin, doxorubicin, methotrexate, temozolomide, 5-FU, dacarbazine and vemurafenib.

In particular embodiments of the invention:
Panicein A hydroquinone is used in combination with at least one of cisplatin, doxorubicin, dacarbazine or vemurafenib,
Panicein C is used in combination with at least one of cisplatin, doxorubicin, dacarbazine or vemurafenib,
Panicein B3 is used in combination with at least one of cisplatin, doxorubicin, dacarbazine or vemurafenib, and
Panicein B2 is used in combination with at least one of cisplatin, doxorubicin, dacarbazine or vemurafenib,
Cisplatin is used in combination with at least one of Panicein A hydroquinone, Panicein C, Panicein B3 and Panicein B2,
Doxorubicin is used in combination with at least one of Panicein A hydroquinone, Panicein C, Panicein B3 and Panicein B2,
Dacarbazine is used in combination with at least one of Panicein A hydroquinone, Panicein C, Panicein B3 and Panicein B2, and
Vemurafenib is used in combination with at least one of Panicein A hydroquinone, Panicein C, Panicein B3 and Panicein B2.

A particular melanoma is a melanoma conventionally treated with dacarbazine (DTIC); cisplatin; B-Raf inhibitors (PLX4032 or vemurafenib); sorafenib and/or temozolomide; electrochemotherapy; or isolated limb perfusion of TNFalpha, in particular of high doses of TNFalpha. In a particular embodiment, the melanoma is a melanoma resistant to the previously described cytotoxic conventional therapies (Jahnke et al. 2014).

A particular breast cancer is a breast cancer conventionally treated with anthracyclins, taxanes, Herceptin, anti-PARP (Poly (ADP-ribose) polymerase), anti-PI3K (Phosphoinositide 3-kinase), mTOR (mammalian Target of Rapamycin) inhibitors, navelbine, gemcitabine, antioestrogens, antiaromatases, and/or a TLR-3 ligand. In a particular embodiment, the breast cancer is a breast cancer resistant to the previously described cytotoxic conventional therapies (Fonseca et al. 2014).

A particular thyroid cancer is a thyroid cancer treated with radioactive iodine or tyrosine kinase inhibitors, preferably RET inhibitors. In a particular embodiment, the thyroid cancer is a thyroid cancer resistant to the previously described cytotoxic conventional therapies (Ma et al. 2014).

A particular prostate cancer is a prostate cancer conventionally treated with taxanes. In a particular embodiment, the prostate cancer is a prostate cancer resistant to taxane (Parks et al. 2014).

A particular colon cancer is a colon cancer conventionally treated with OXP and/or the combination of 5-fluorouracil (5 FU) and folinic acid. In a particular embodiment, the colon cancer is a colon cancer resistant to the previously described cytotoxic conventional therapies (Kolosenko et al. 2014).

A particular metastatic colon cancer is a metastatic colon cancer conventionally treated with 5 FU and OXP or irinothecan.

A particular rectal cancer is a rectal cancer conventionally treated with CDDP and/or 5 FU. In a particular embodiment, the rectal cancer is a rectal carcinoma resistant to the previously described cytotoxic conventional therapies (Fan et al. 2013).

A particular oesophagus cancer is an oesophagus cancer treated with CDDP, typically a oesophagus cancer resistant to CDDP.

A particular lung cancer is a lung cancer conventionally treated with platine or Permetrexed (Alimta®).

A particular early stage Non Small Cell Lung Cancer (NSCLC) is an NSCLC conventionally treated with CDDP and/or etoposide, or with taxanes and avastin [anti-VEGF (Vascular endothelial growth factor) antibody].

In a particular embodiment, the lung cancer is a NSCLC resistant to the previously described cytotoxic conventional therapies (Cheng and Chen 2014).

A particular osteosarcoma is conventionally treated with anthracyclins, imatinib (Gleevec®). In a particular embodiment, the osteosarcoma is a osteosarcoma resistant to the previously described cytotoxic conventional therapies (Duan et al. 2014).

A particular neuroblastoma is a neuroblastoma conventionally treated with anthracyclines or alkylating agents, in particular in the context of autologous bone marrow transplantation or of stem cells transplantation. In a particular embodiment, the neuroblastoma is resistant to anthracyclines or alkylating agents.

A particular leukemia is a lymphoid leukemia or a myeloid leukemia conventionally treated with azacitidine. In a particular embodiment, the leukemia is resistant to cytotoxic conventional therapies (Lehmann-Che et al. 2014).

A particular acute lymphoid leukemia is an acute lymphoid leukemia treated with anthracyclins, vinblastine and/or vincristine, typically an acute lymphoid leukemia resistant to anthracyclins, vinblastine and/or vincristine.

A particular multiple myeloma is a malignant hemopathy conventionally treated with anthracyclins, bortezomiv, revlimide, thalidomide and/or an alkylating agent, in particular in the context of autologous bone marrow or stem cell transplantation. In a particular embodiment, the multiple myeloma is a multiple myeloma resistant to the previously described cytotoxic conventional therapies (Blotta et al. 2012).

A particular glioma is a frequent and devastating primary malignant brain tumor in adults conventionally treated with temozolomide, procarbazine, iomustine or methotrexate. In a particular embodiment, the glioma is a glioma resistant to the previously described cytotoxic conventional therapies.

A particular glioblastoma is a glioblastoma conventionally treated with temozolomide. In a particular embodiment, the glioblastoma is resistant to cytotoxic conventional therapies (Wu et al. 2014).

A particular adrenocortical carcinoma is a rare carcinoma conventionally treated with a combination of chemotherapeutic agents (etoposide, doxorubicin and cisplatin) and an adrenolytic substance (mitonane). In a particular embodiment, the adrenocortical carcinoma is resistant to cytotoxic conventional therapies.

A particular pancreatic cancer is a pancreatic cancer conventionally treated with gemcitabine. In a particular embodiment, the pancreatic cancer is resistant to the previously described cytotoxic conventional therapy (Zhu et al. 2012).

A particular ovarian cancer is an ovarian cancer conventionally treated with platinum-based chemotherapy such as cisplatin. In a particular embodiment, the ovarian cancer is resistant to platinum-based chemotherapy (He et al. 2014).

The present disclosure further relates to use of a compound of the invention as defined above (including any one of the disclosed embodiments) to prepare a pharmaceutical composition or medicament, said composition being capable of allowing or of improving the efficiency of a therapy of cancer in a subject in need thereof The compound of the invention can in particular be advantageously used, in combination with at least one chemotherapeutic drug or any other therapeutically active compound, for treating cancer, for preventing cancer metastasis and/or for preventing cancer recurrence in a subject.

A preferred pharmaceutical composition thus comprises, as a combined preparation, at least one drug used in a treatment of a cancer, typically at least one chemotherapeutic drug as herein described or any other therapeutically active compound, for simultaneous, separate or sequential use in the treatment of said cancer.

The other therapeutically active compounds can for example be selected from a statin, an antagonist of the Smoothened receptor and an antagonist of the GLI1 transcription factor.

Herein described are also (i) a method for preventing or treating cancer, (ii) a method for increasing the sensitivity of a cancer to a chemotherapeutic agent, and (iii) a method for decreasing the resistance of a cancer with respect to a chemotherapeutic agent, each of said methods comprising administering to a subject in need thereof with an effective amount of at least one compound of formula (I) as defined above including any one of the disclosed embodiments or a pharmaceutical composition as defined above, preferably together with a chemotherapeutic drug classically used in the prevention or treatment of cancer as herein described (as a combined preparation).

In another particular embodiment, said method further comprises administering an effective amount of another therapeutically active compound for preventing or treating cancer or a cancer treatment side effect.

By "treatment" is meant the curative treatment of cancer. A curative treatment is defined as a treatment that completely treat (cure) or partially treat (induces tumor growth stabilization, retardation or regression) cancer.

As used herein, "a therapeutically effective amount or dose" refers to an amount of the compound of the invention which prevents, removes, slows down the cancer or reduces or delays one or several symptoms or disorders caused by or associated with said disease in the subject, preferably a human being. The effective amount, and more generally the dosage regimen, of the compound of the invention and pharmaceutical compositions thereof may be determined and adapted by the one skilled in the art. An effective dose can be determined by the use of conventional techniques and by observing results obtained under analogous circumstances. The therapeutically effective dose of the compound of the invention will vary depending on the disease to be treated or prevented, its gravity, the route of administration, any co-therapy involved, the patient's age, weight, general medical condition, medical history, etc.

Typically, the amount of the compound to be administrated to a patient may range from about 0.01 to 500 mg/kg of body weight for a human patient. In a particular embodiment, the pharmaceutical composition according to the invention comprises 0.01 mg/kg to 300 mg/kg of the compound of the invention, for instance from 25 to 300 mg/kg.

In a particular aspect, the compounds of the invention can be administered to the subject by parenteral route, oral route or intravenous (IV) injection. The compound or the nanoparticle of the invention may be administered to the subject daily (for example 1, 2, 3, 4, 5, 6 or 7 times a day) during several consecutive days, for example during 2 to 10 consecutive days, preferably from 3 to 6 consecutive days. Said treatment may be repeated during 1, 2, 3, 4, 5, 6 or 7 weeks, or every two or three weeks or every one, two or three months. Alternatively, several treatment cycles can be performed, optionally with a break period between two treatment cycles, for instance of 1, 2, 3, 4 or 5 weeks. The compound or the nanoparticle of the invention can for example be administered as a single dose once a week, once every two weeks, or once a month. The treatment may be repeated one or several times per year.

Doses are administered at appropriate intervals which can be determined by the skilled person. The amount chosen will depend on multiple factors, including the route of administration, duration of administration, time of administration, the elimination rate of the selected compound of formula (I), or of the various products used in combination with said compound, the age, weight and physical condition of the patient and his/her medical history, and any other information known in medicine.

The administration route can be oral or parenteral, typically rectal, sublingual, intranasal, intra-peritoneal (IP), intra-venous (IV), intra-arterial (IA), intra-muscular (IM), intra-cerebellar, intrathecal, intratumoral and/or intradermal. The pharmaceutical composition is adapted for one or several of the above-mentioned routes. The pharmaceutical composition is preferably administered by injection or by intravenous infusion of suitable sterile solutions, or in the form of liquid or solid doses via the alimentary canal.

The pharmaceutical composition can be formulated as solutions in pharmaceutically compatible solvents or as gels, oils, emulsions, suspensions, or dispersions in suitable pharmaceutical solvents or vehicles, or as pills, tablets, capsules, powders, suppositories, etc. that contain solid vehicles in a way known in the art, possibly through dosage forms or devices providing sustained and/or delayed release. For this type of formulation, an agent such as cellulose, lipids, carbonates or starches are used advantageously.

Agents or vehicles that can be used in the formulations (liquid and/or injectable and/or solid) are excipients or inert vehicles, i.e. pharmaceutically inactive and non-toxic vehicles.

Mention may be made, for example, of saline, physiological, isotonic and/or buffered solutions, compatible with pharmaceutical use and known to those skilled in the art. The compositions may contain one or more agents or vehicles chosen from dispersants, solubilizers, stabilizers, preservatives, etc.

Particular examples are methylcellulose, hydroxymethylcellulose, carboxymethylcellulose, cyclodextrins, polysorbate 80, mannitol, gelatin, lactose, liposomes, vegetable oils or animal, acacia, etc. Preferably, vegetable oils are used.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations suitable for parenteral administration conveniently comprise a sterile oily or aqueous preparation of the active ingredient which is preferably isotonic with the blood of the recipient. Every such formulation can also contain other pharmaceutically compatible and non-toxic auxiliary agents, such as, e.g. stabilizers, antioxidants, binders, dyes, emulsifiers or flavouring substances.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof. The pharmaceutical compositions are advantageously applied by injection or intravenous infusion of suitable sterile solutions or as oral dosage by the digestive tract. Methods for the safe and effective administration of most of these chemotherapeutic agents are known to those skilled in the art. In addition, their administration is described in the standard literature.

Another object of the invention is a kit comprising at least one compound of formula (I) according to the invention and preferably at least one chemotherapeutic drug in distinct containers. The kit can further comprise instructions for preparing a composition according to the invention, for carrying out any one of the herein described method, for example for preventing or treating cancer, for preventing or treating cancer metastasis and/or for preventing or treating cancer recurrence in a subject.

In a particular embodiment, the present invention relates to the use of a kit according to the invention to prepare a composition as herein described.

In another particular embodiment, the kit is suitable for implementing any one of the herein described method, in particular a method for treating cancer, for preventing cancer metastasis and/or for preventing cancer recurrence in a subject.

Further aspects and advantages of the present invention will be disclosed in the following experimental section which shall be considered as illustrative only.

LEGENDS TO THE FIGURES

The patent or application file contains at least one drawing executed in color. Copies of this patent or patent application publication, with color drawing(s), will be provided by the Office upon request and payment of the necessary fee.

FIG. 1: Patched: new therapeutic target for cancer treatment

Schematic representation of the activity of efflux of chemotherapeutic agent of Patched. Dxr: doxorubicin, CSC: cancer stem cell.

Figure 2:
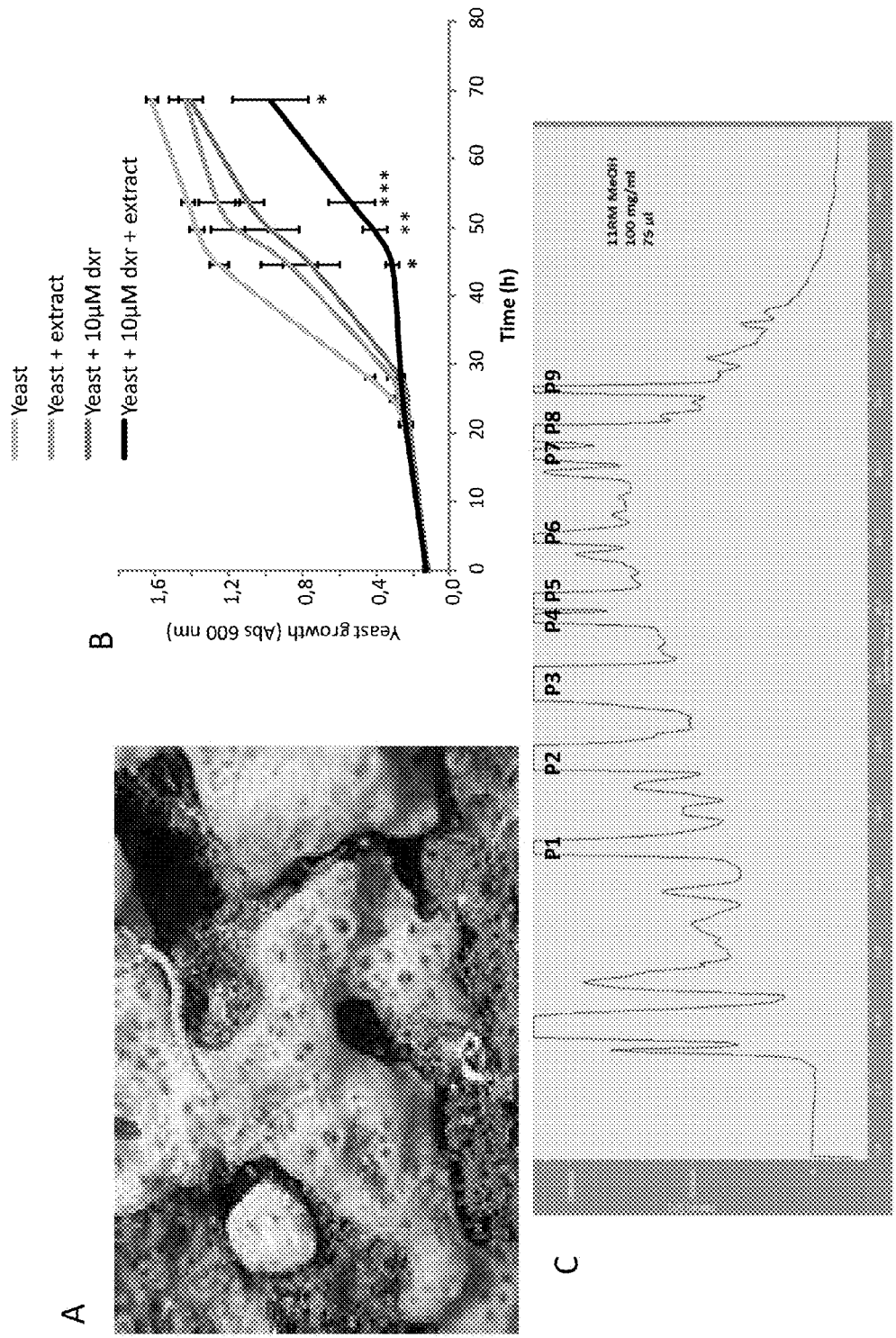
Figure 2:
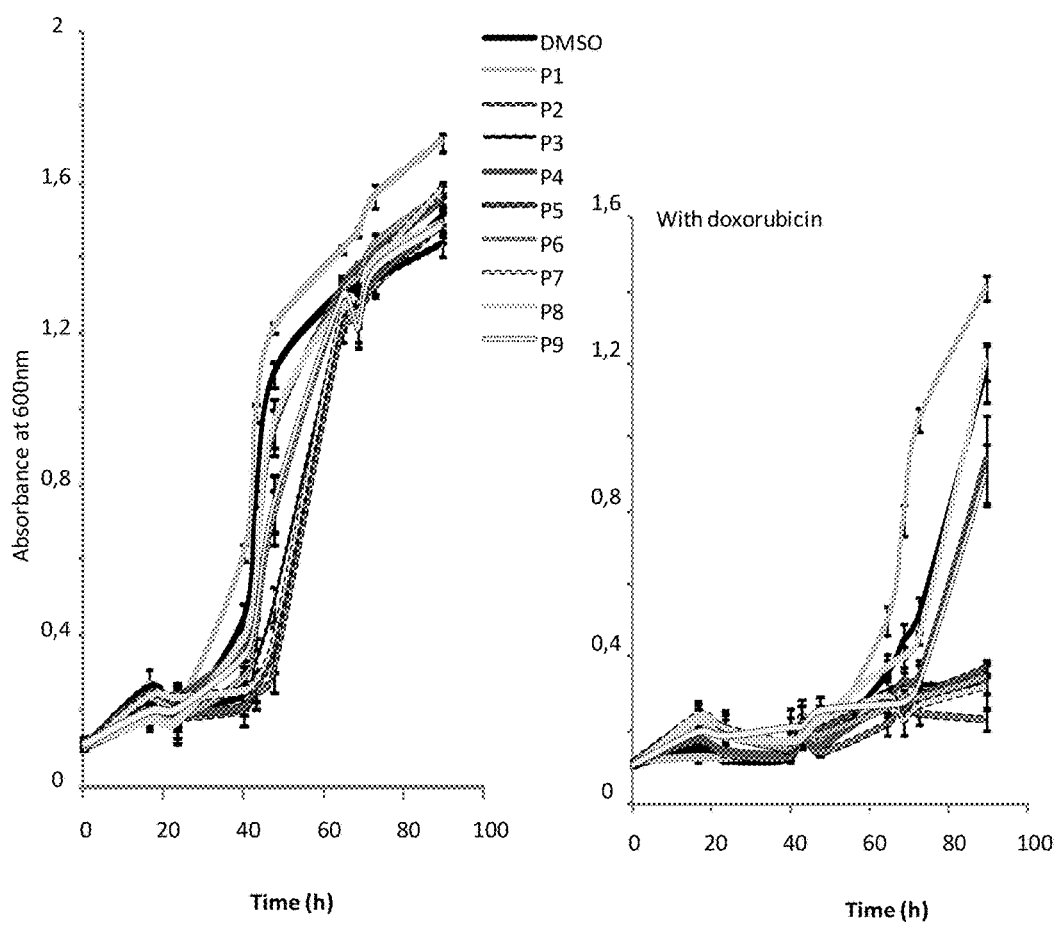

FIG. 2: *Haliclona mucosa* extract inhibits resistance of human Patched expressing yeast to doxorubicin A. *Haliclona mucosa* sponge. B. *Haliclona mucosa* methanolic fraction contains inhibitors of the resistance of Patched-expressing yeasts to doxorubicin. Yeast *S. cerevisiae* expressing hPtc were grown in 96 well plates in the presence of 10 µg/mL of the methanolic fraction of *Haliclona mucosa* crude extract dissolved in DMSO and in presence or not of 10 µM of doxorubicin (dxr). The growth of yeasts was measured by absorbance at 600 nm and the results shown are the mean of three independent experiments. C. Purification profile of *Haliclona mucosa* methanolic fraction. A preparative phenyl-hexyl HPLC column was used with a gradient starting at (47 H20: 53 ACN: 0.1 TFA) to (0 H20: 100 ACN: 0.1 TFA), flow rate: 10.0 mL/min, injection volume: 75 µl at 100 mg/mL. D. Five of the compounds purified from *Haliclona mucosa* methanolic fraction strongly inhibit the resistance of hPtc-expressing yeasts to dxr. Purified compounds dissolved in DMSO were added (at 10 µg/mL) to the growth medium containing or not 10 µM dxr. The growth of yeasts was measured by absorbance at 600 nm.

Figure 3:
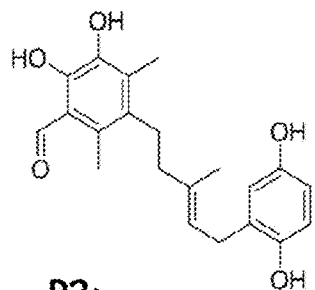
Figure 3:
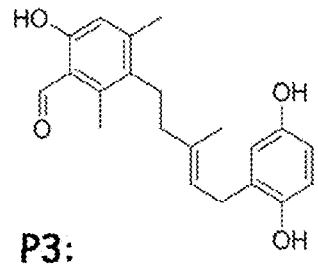
Figure 3:
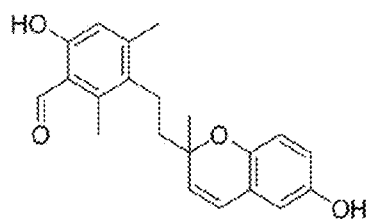
Figure 3:
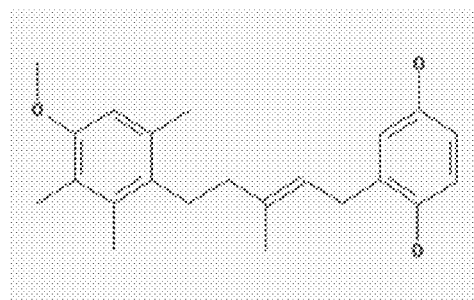

FIG. 3: Structure of compounds P2 (panicein C), P3 (panicein B3), P4 (panicein B2) and P5 (panicein A hydroquinone).

Figure 4:
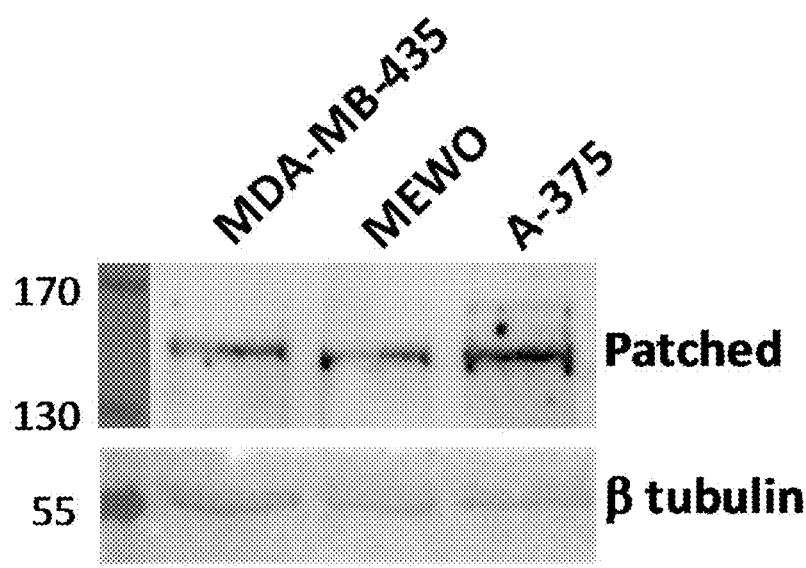
Figure 4:
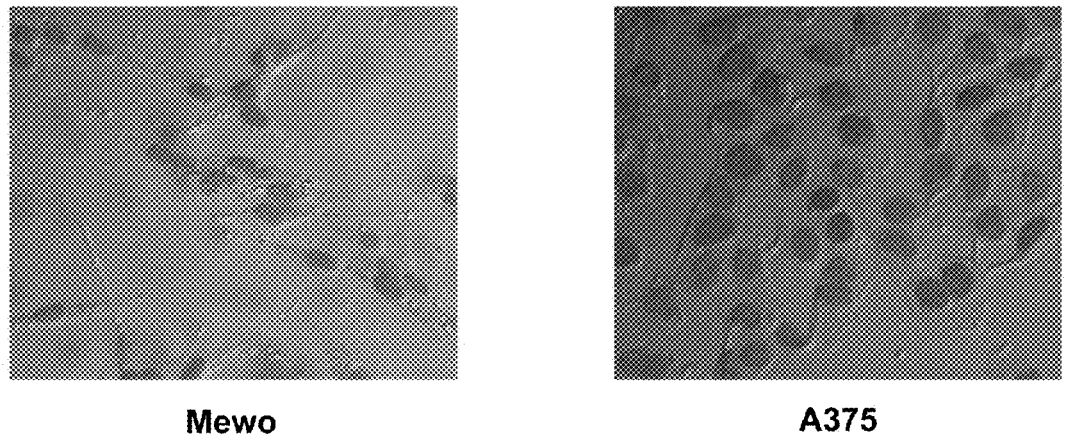

FIG. 4: Melanoma cells over-express Patched protein.

A. Western-blotting with rabbit anti-Patched antibodies (1/1000) on total extracts from three different melanoma cell lines (MDA-MB-435, MeWo and A375). Patched is expected at 150 KDa. (β tubulin was used as loading control. B. Immuno-labeling of MeWo and A375 using Patched antibodies (1/200) and rhodamine-anti-rabbit antibodies. Patched labeling (in red) was superimposed to DAPI (in blue) and image of the cells in visible light. Rhodamine-anti-rabbit antibodies alone did not give any signal on these cells (not shown).

Figure 5:
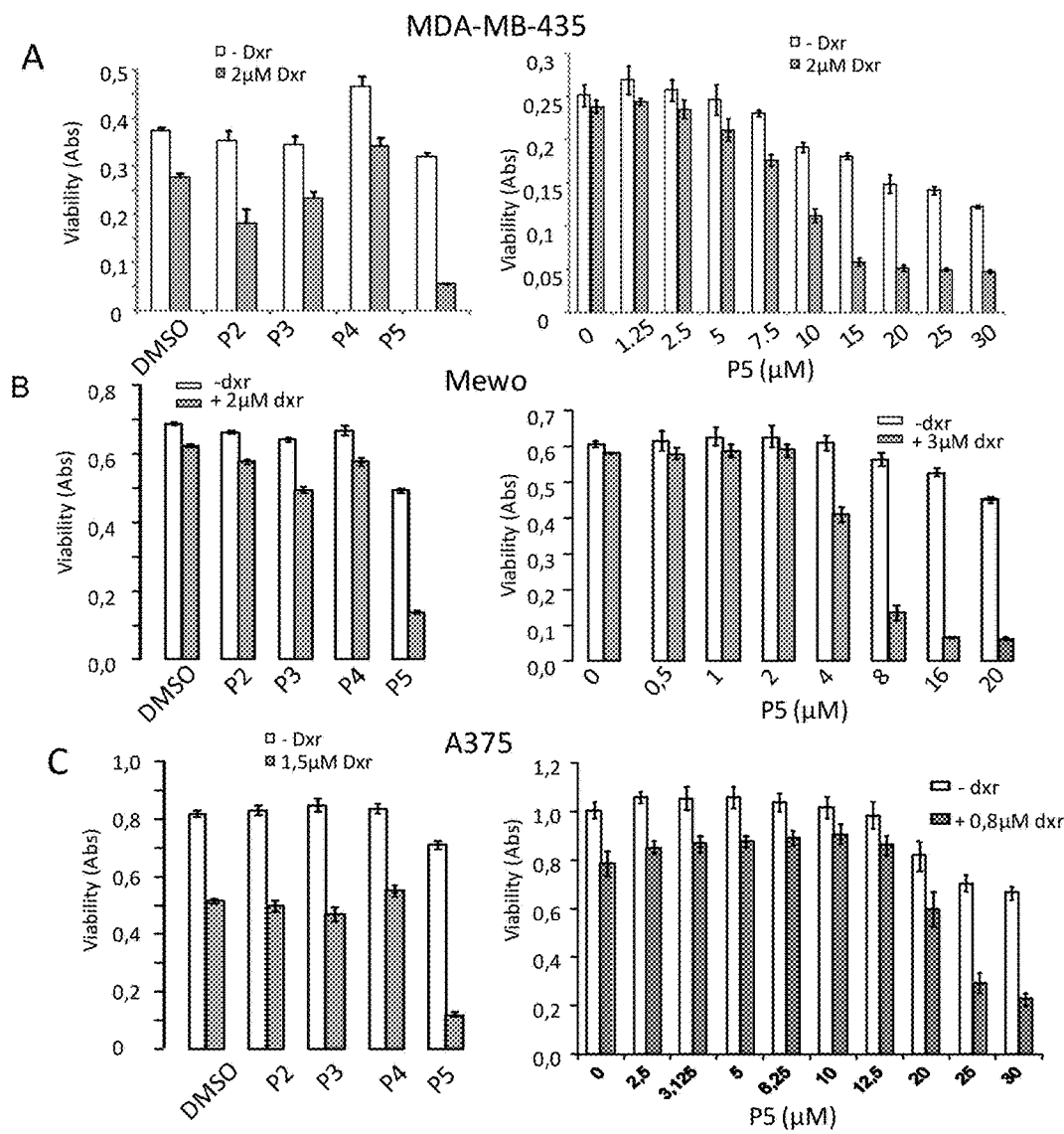
Figure 5:
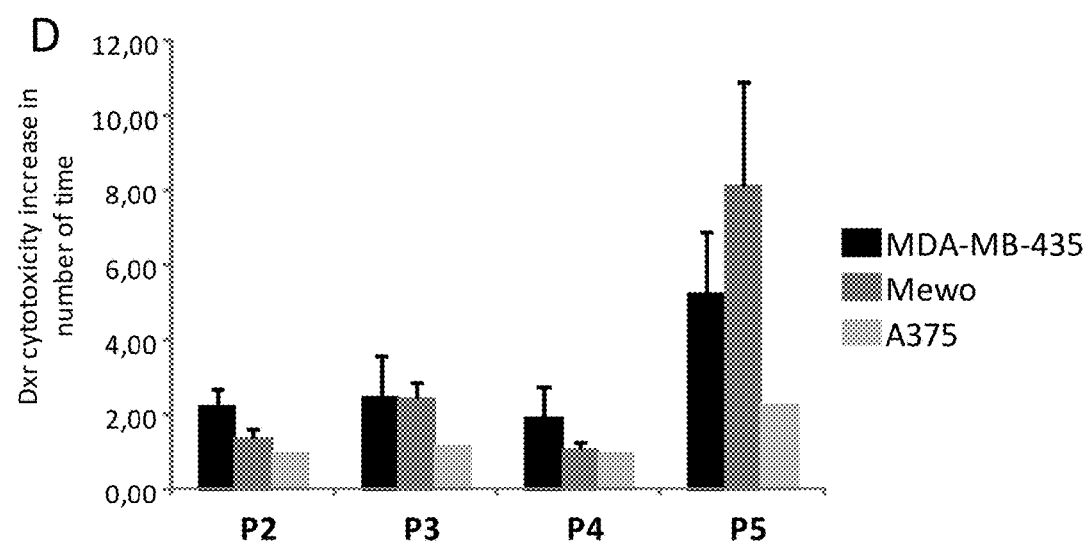

FIG. 5: Paniceins increase doxorubicin cytotoxicity for melanoma cells.

Cells were grown in 96 well plates in complete DMEM medium to achieve 60% to 70% confluence. Medium was then removed and replaced with 100 μL/well of complete DMEM medium containing paniceins at 10 μM (or at increasing concentrations for EC50 measurement) or DMSO as control. After 2 hours, 100 μL of complete DMEM medium containing doxorubicin was added in half wells to obtain the final concentration of 2 μM for MDA-MB-435 and MeWo, and 1.5 μM for A375. The cell viability was measured after 24 hours. Effect of compounds P2, P3, P4 and P5 on cell viability, and dose-response for compound P5 are shown for MDA-MB-435 (A), MeWo (B) and A375 (C). D. Enhancement of dxr cytotoxicity by paniceins is represented. The means (+/−sem) of at least three independent experiments are reported.

Figure 6:
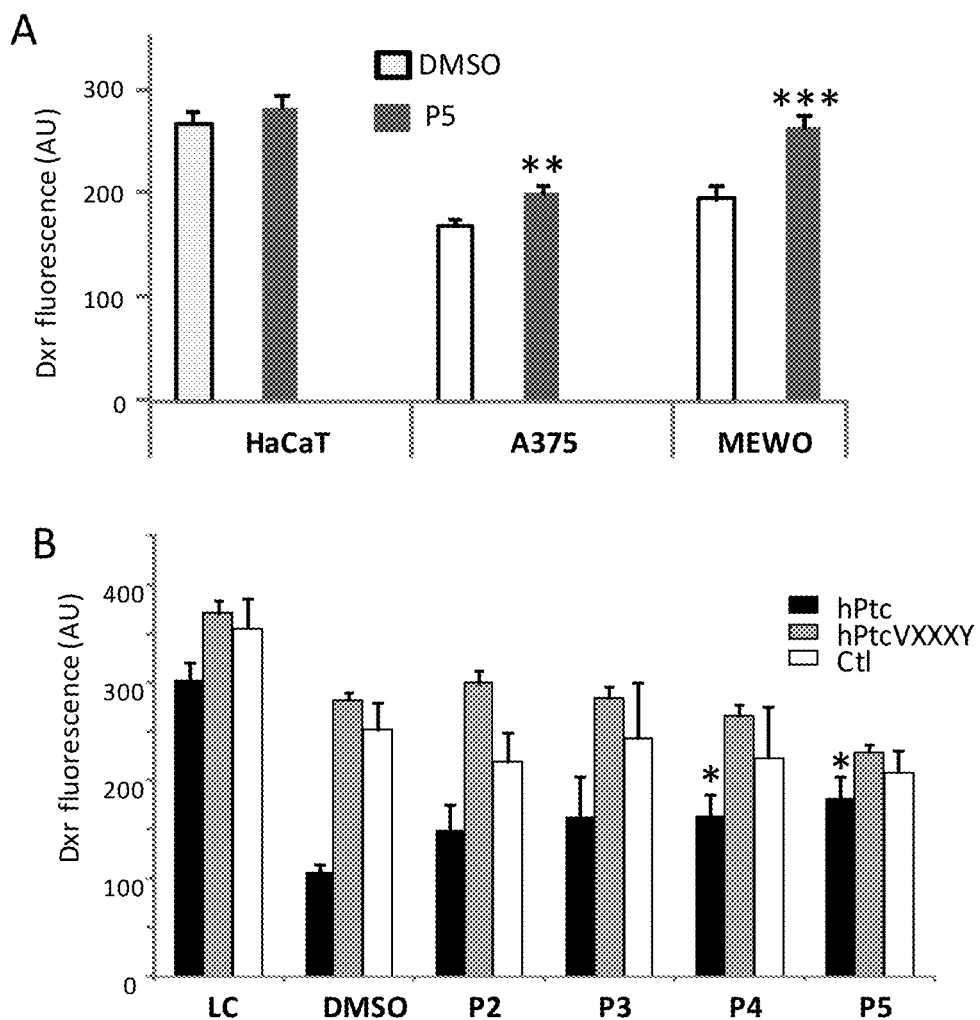

FIG. 6: Paniceins inhibit doxorubicin efflux.

A. Compound P5 inhibits doxorubicin efflux from melanoma cells MeWo and A375. Cells were grown on cover-slips, incubated for 2 hour at 37° C. with 10 μM doxorubicin and quickly rinsed with phosphate buffer (pH 7.4). One cover-slip of each cell line was immediately fixed for doxorubicin charge control. The other cover-slips were incubated with buffer supplemented with DMSO or 10 μM of compound P5 30 min under gentle shaking and immediately fixed. Dxr intracellular fluorescence was visualized by epifluorescence and analyzed using Image J software on more than 30 cells of 3 different fields for each condition. The results were analyzed using the Student t test in which significance is attained at $P<0.05$ (: $P<0.005$, *: $P<0.0005$). B. Paniceins inhibit doxorubicin efflux from Patched-expressing yeasts. Yeasts expressing wild-type Patched (hPtc, in black), mutant Patched G509VD513Y (hPtcVXXXY, in grey), and control yeasts (in white) were incubated in buffer supplemented with 5 mM of 2-deoxy-D-glucose and 10 μM dxr for 2 hours at 4° C. After centrifugation and supernatant removing, one sample was immediately fixed for charge control and the other samples were resuspended in buffer containing 5 mM of 2-deoxy-D-glucose supplemented with DMSO or 10 μM of paniceins 10 minutes at 25° C. with gentle shaking. After centrifugation and supernatant removing, samples were fixed and deposited on coverslips for epifluorescence microscopy observation. Dxr intracellular fluorescence quantification was carried out using Image J software on more than 30 yeasts on 3 different fields for each condition. The results were analyzed using the Student t test in which significance is attained at $P<0.05$ (*).

Figure 7:
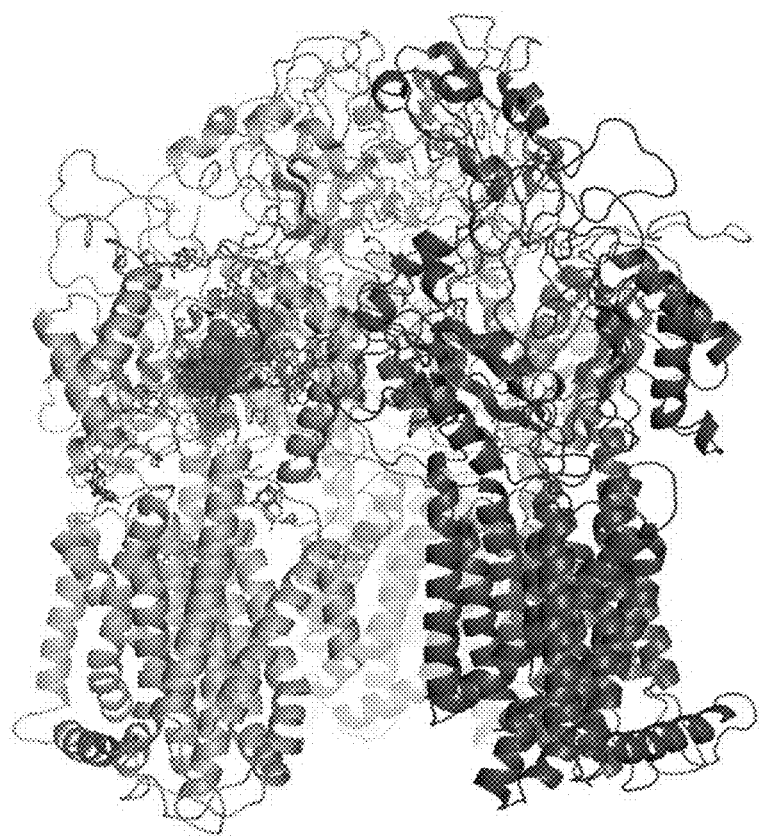

FIG. 7: Panicein A hydroquinone presents a strong docking cluster close to the doxorubin binding site in Patched structural model.

A model of Patched structure has been done on the bases of the crystal structure of AcrB, the principal multidrug efflux transporter from the RND family in *Escherichia coli* describes with and without doxorubicin by Murakami et al (Nature 2006). The AcrB-drug complex consists of three protomers. Dxr was found in the periplasmic domain of one of the three protomers. Docking of Panicein A hydroquinone into the model structure of Patched shows a strong probability of binding in a cluster close to the dxr binding site.

Figure 8:
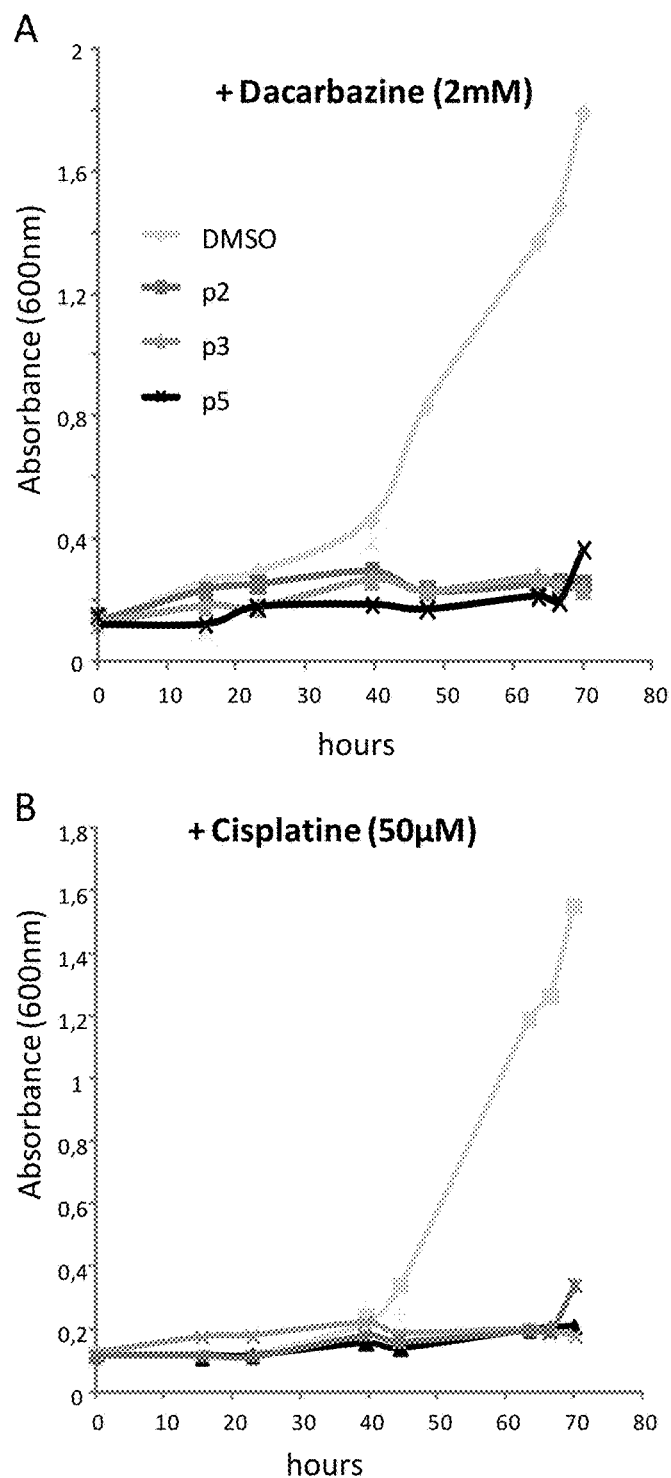
Figure 8:
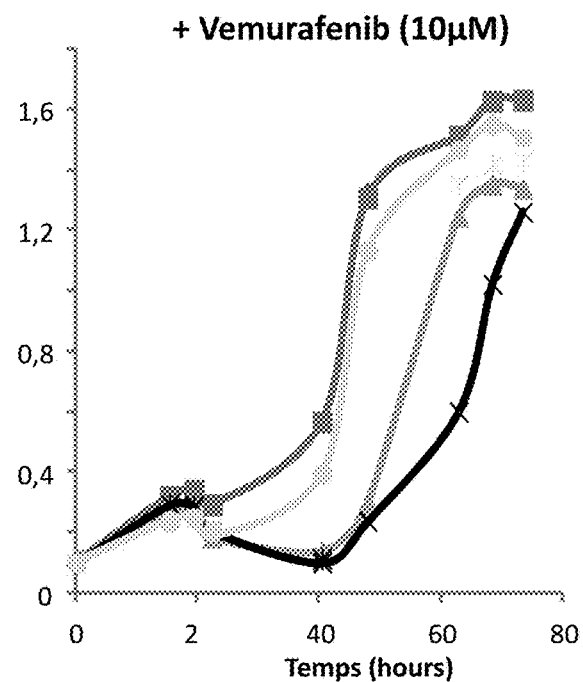
Figure 8:
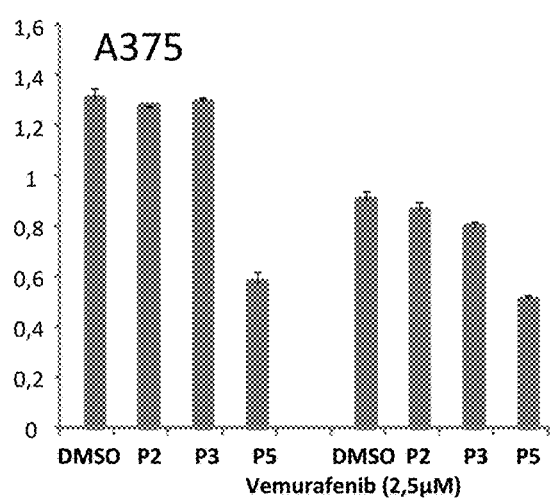

FIG. 8: Paniceins inhibit resistance to other chemotherapeutic agents.

Paniceins were added at a final concentration of 10 μM to the yeast growth medium containing 2 mM of dacarbazine (A), 50 μM of cisplatine (B), or 10 μM of vemurafenib (C). The growth of hPtc-expressing-yeasts was measured by absorbance at 600 nm. (D) Viability test using neutral red shows that panicein A hydroquinone (10 μM) strongly increases vemurafenib cytotoxicity for A375 melanoma cells.

Figure 9:
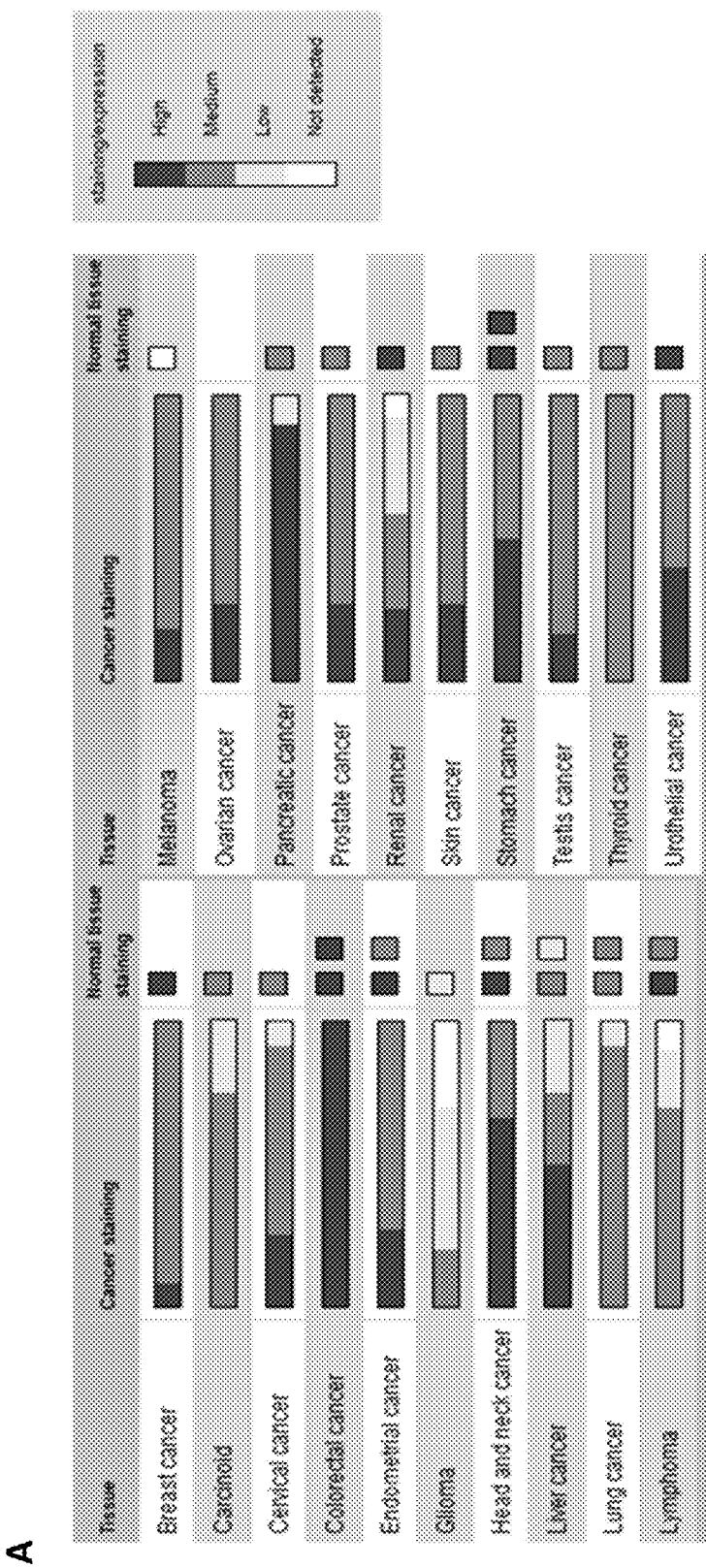
Figure 9:
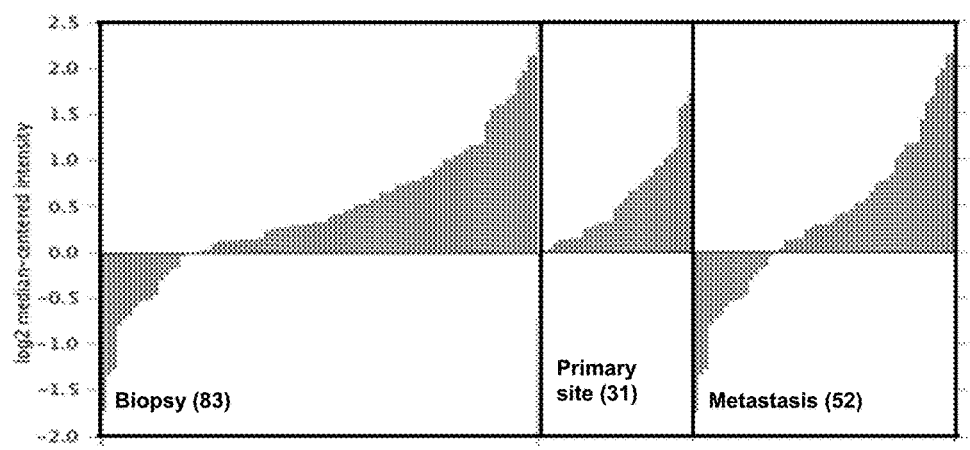

FIG. 9: Expression of Patched in Melanoma. (a) Patched protein is expressed in different cancers (IHC on tissue, data extracted from the Human Protein Atlas web site). (b) Patched mRNAs in 154 melanoma samples (data extracted from ONCOMINE web site).

Figure 10:
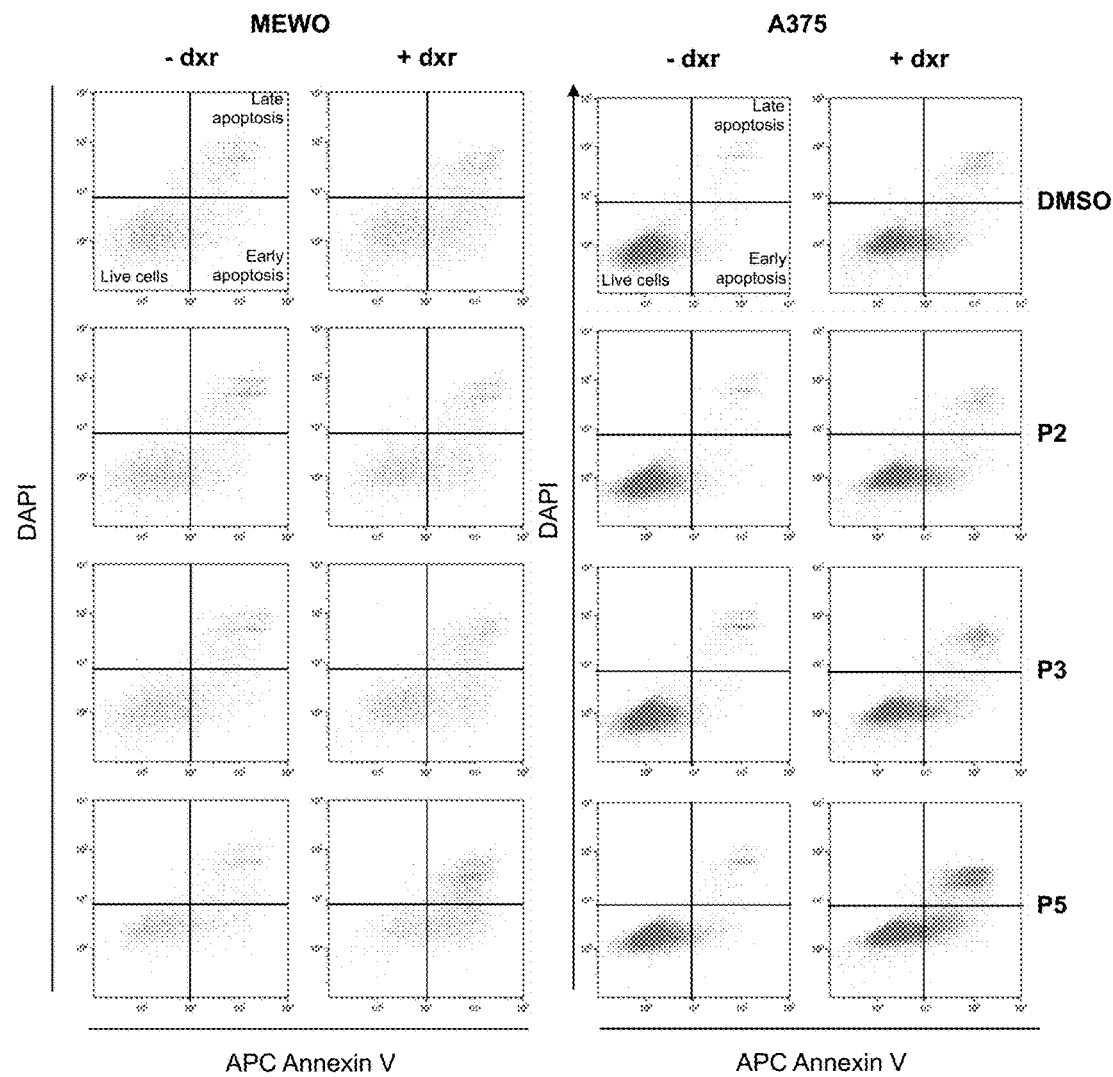
Figure 10:
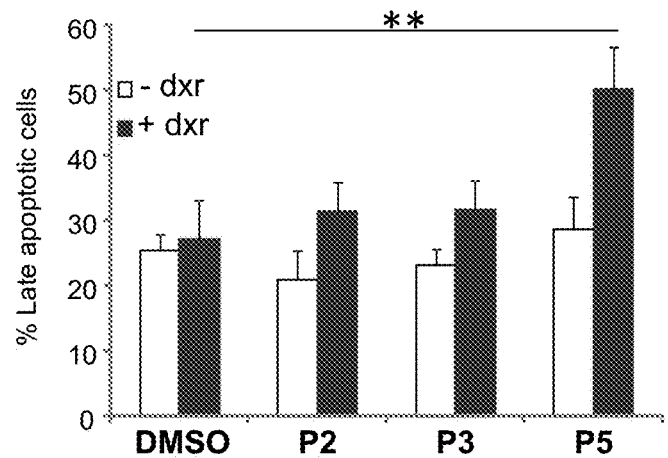
Figure 10:
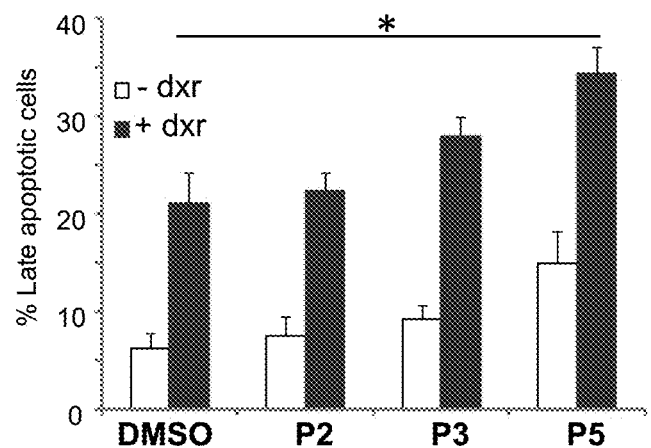

FIG. 10: Panicein A hydroquinone strongly increases the number of apoptotic melanoma cells Cells were sampled after 24 h treatment with DMSO, paniceins and/or dxr, and apoptosis determined via AnnexinV and DAPI co-staining. Cells in early apoptosis are AnnexinV positive and DAPI negative, and cells in late apoptosis are AnnexinV and DAPI double positive. Histograms represent the mean percentage (+/−SEM) of cells in late apoptosis from three independent experiments and were analyzed using the Student t-test in which significance is attained at $P<0.05$ (*) (**: $P<0.005$).

Figure 11:
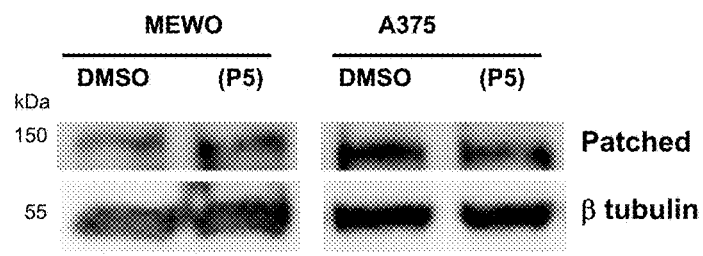

FIG. 11: Panicein A hydroquinone does not affect Patched protein expression or stability. Western-blotting on total extracts from MEWO and A375 cells after 24 h treatment with 10 μM of panicein A hydroquinone (P5) or with DMSO.

Figure 12:
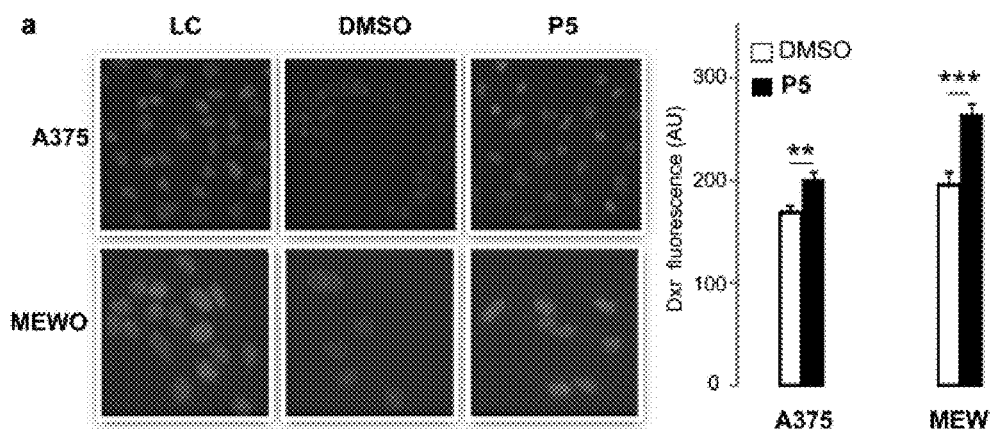
Figure 12:
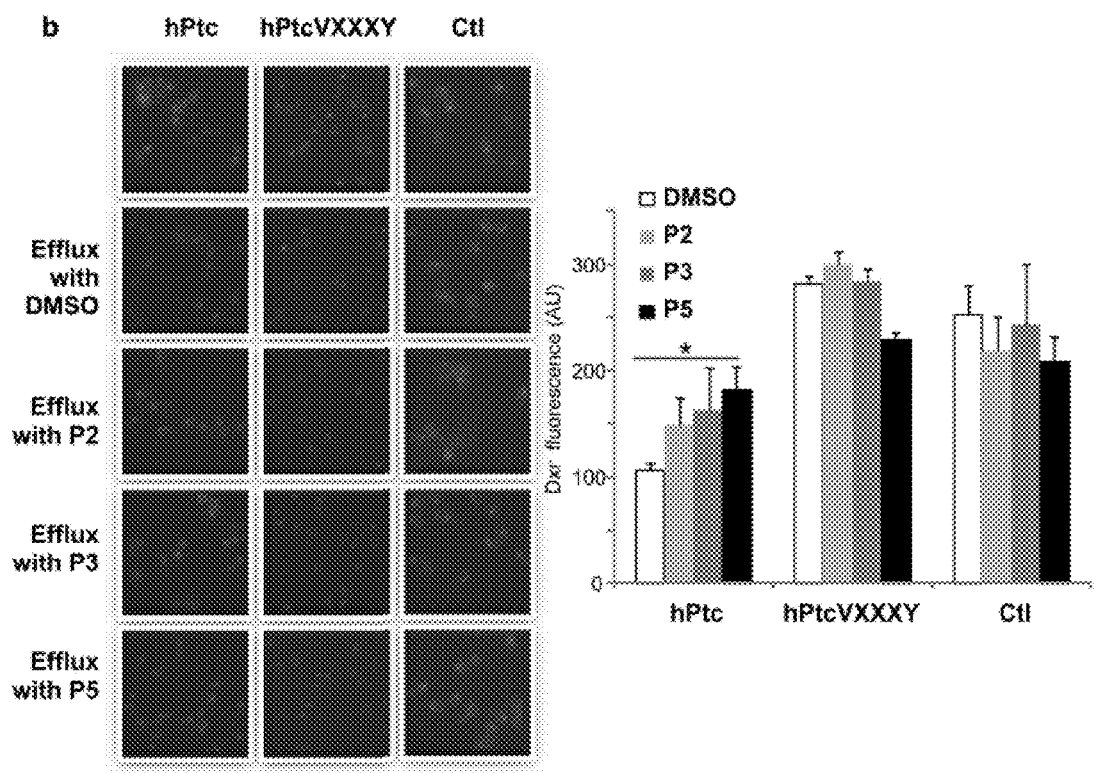

FIG. 12: This figure reports the same experiment as FIG. 6 with the fluorescence images of melanoma cells (A) and yeast (B). A. Compound P5 inhibits doxorubicin efflux from melanoma cells MeWo and A375. Cells were grown on cover-slips, incubated for 2 hour at 37° C. with 10 μM doxorubicin and quickly rinsed with phosphate buffer (pH 7.4). One cover-slip of each cell line was immediately fixed for doxorubicin charge control. The other cover-slips were incubated with buffer supplemented with DMSO or 10 μM of compound P5 30 min under gentle shaking and immediately fixed. Dxr intracellular fluorescence was visualized by epifluorescence (left part) and analyzed using Image J software on more than 30 cells of 3 different fields for each condition. The results were analyzed using the Student t test in which significance is attained at $P<0.05$ (: $P<0.005$, *: $P<0.0005$) (right part). B. Paniceins inhibit doxorubicin efflux from Patched-expressing yeasts. Yeasts expressing wild-type Patched (hPtc, in black), mutant Patched G509VD513Y (hPtcVXXXY, in grey), and control yeasts (in white) were incubated in buffer supplemented with 5 mM of 2-deoxy-D-glucose and 10 μM dxr for 2 hours at 4° C. After centrifugation and supernatant removing, one sample was immediately fixed for charge control and the other samples were resuspended in buffer containing 5 mM of 2-deoxy-D-glucose supplemented with DMSO or 10 μM of paniceins 10 minutes at 25° C. with gentle shaking. After centrifugation and supernatant removing, samples were fixed and deposited on coverslips for epifluorescence microscopy observation (left part). Dxr intracellular fluorescence quantification was carried out using Image J software on more than 30 yeasts on 3 different fields for each condition. The results were analyzed using the Student t test in which significance is attained at P<0.05 (*) (right part).

EXAMPLES

Biological Material

Specimens of *Haliclona mucosa* were collected in February-May 2013 by hand using SCUBA diving in the rade de Villefranche-sur-Mer (France), at depths ranging from 20 or 40 m in obscure cavities or caves, and kept frozen until used.

Human melanoma cell lines Mewo and A375 were purchased from ATCC and MDA-MB-435 were obtained from C. Vandier, initially purchased from the ATCC. The three cell lines were grown in DMEM medium supplemented with 10% FBS, 100 U/mL penicillin, and 100 mg/mL streptomycin, at 37° C. in a 5% $CO_2$/95% air water-saturated atmosphere.

K699 *Saccharomyces cerevisiae* yeast strain (Mata, ura3, and leu 2-3, kindly donated by R. Arkowitz) were transformed with pYEP-hPtc-MAP (human Patched over-expression), pYEP-mMyo-MAP (control), or pYEP-hPtcG509VD513Y-MAP (mutant Patched expression) expression vector and grown as described (Bidet et al. 2011) at 18° C. until an OD at 600 nm between 5 and 7.

Screening Test 1: Effect of Sponge Extracts on the Resistance of Yeast-Expressing Patched to Doxorubicin.

*S. cerevisiae* expressing human Patched were grown in 10 mL of minimal medium (supplemented with 2% of glucose and amino acids cocktail without leucine) at 30° C. When the exponential phase was obtained (OD600=5-7), yeasts were precultured in the same medium to OD600=1-2. Yeasts were then diluted in rich medium containing 2% of glucose in 96-well plates. Methanolic or purified fractions (at 10 µg/mL final concentration) were added in all wells, and doxorubicin (10 µM final concentration) was added in half of the wells. Plates were incubated at 18° C. on a shaker at 1250 rpm (microtitre plate shaker SSL5 Stuart) and absorbance at 600 nm was recorded for about 72 hours.

Screening Test 2: Effect of Sponges Fractions on Doxorubicin Cytotoxicity.

Melanoma cells MDA-MB-435, Mewo and A375 were seeded on 96-well plates and grown 48 hours in complete DMEM medium to achieve 60% to 70% confluence. Medium was then removed and replaced with 100 µL/well of complete DMEM medium containing the compounds of interest at defined concentration or DMSO as control. After 2 hours, 1004 of complete DMEM medium containing doxorubicin was added in half wells to obtain 2 µM doxorubicin. Plates were incubated at 37° C. in a 5% CO2/95% air water-saturated atmosphere. After 24 hours, microplates were incubated 3 hours at 37° C. with 100 µL/wells neutral red (NR) solution (50 µg/mL in DMEM). After a rapid wash with PBS at 4° C., microplates were gently tapped several times on absorbent paper. Cells were solubilized with 100 µL of a solution containing 1% acetic acid, 49% $H_2O$, 50% ethanol by vortexing 3 minutes at 700 rpm and the absorbance at 600 nm was measured. EC50 were calculated using Regressi software.

Protein Quantification

Protein concentrations were determined by the Bradford method using a Bio-Rad kit.

SDS-PAGE and Western Blotting

Total extracts from melanoma cells were prepared. Samples were separated on 8% SDS-PAGE and transferred to nitrocellulose membranes (Amersham) using standard techniques. After 1 hour at room temperature in blocking buffer (20 mmol/L Tris-HCl pH 7.5, 450 mmol/L NaCl, 0.1% Tween-20, and 4% non-fat milk), nitrocellulose membranes were incubated overnight at 4° C. with rabbit anti-Patched antiserum (Ab130.6 1:1000 generous gift from M. Ruat or Ab39266 from Abcam 1/1000) and monoclonal mouse anti-βtubulin antibody (Sigma; 1/1000). After 3 washes, membranes were incubated 45 min with anti-mouse (1:5000) or anti-rabbit (1:3000) immunoglobulin coupled to horseradish peroxidase (Dako). Detection was carried out with an ECL kit (Millipore) on a Las3000 (Fuji).

Drug Efflux Measurements

On melanoma cells: For doxorubicin incorporation in melanoma cells, the protocol was adapted from Bidet et al. (2012). Cells were seeded on coverslips in 12-well plates and allowed to grow to 80% confluence. Coverslips were incubated 2 hours at 37° C. with doxorubicin (10 µM) in physiological buffer (140 mM NaCl, 5 mM KCl, 1 mM CaCl2, 1 mM MgSO4, 5 mM glucose, 20 mM HEPES, pH 7.4) and quickly rinsed with phosphate buffer (pH 7.4). One coverslip of each cell line was immediately fixed 10 minutes with 4% paraformaldehyde (Sigma) for doxorubicin charge control. The other coverslips were incubated with physiological buffer supplemented with DMSO or 10 µM of paniceins 30 min under gentle shaking at 37° C., and immediately fixed with 4% paraformaldehyde. Coverslips were observed by epifluorescence microscopy using an objective 40× and filters for Alexa 594 probe. Quantification of doxorubicin intracellular fluorescence was carried out using Image J software on more than 30 cells of 3 different fields for each condition. The results were analyzed using the Student t test in which significance is attained at P<0.05.

On yeasts: Yeasts expressing Patched (hPtc), mutant Patched (hPtcG509VD513Y), or control yeasts were washed with cold water, resuspended at an OD600 of 10 in Hepes-NaOH buffer (pH 7.0) supplemented with 5 mM of 2-deoxy-D-glucose, and incubated with 10 µM doxorubicin for 2 hours at 4° C. in the cold room on a rotating wheel protected from light. Yeasts were centrifuged and the supernatant was removed. One sample was immediately fixed with 4% paraformaldehyde for doxorubicin loading control. The other samples were resuspended in Hepes-NaOH buffer (pH 7.0) containing 5 mM of 2-deoxy-D-glucose supplemented with DMSO or 10 µM of paniceins, and incubated 10 minutes at 20° C. with gentle shaking in a Benchmark Multi-therm shaker protected from light. Samples were centrifuged for 1 minute at 18,000 g, supernatants were removed and yeasts were fixed with 4% paraformaldehyde. 10 µL of each sample were deposited on a coverslip and observed by epifluorescence microscopy using an objective 63x and filters for Alexa 594. Quantification of doxorubicin intracellular fluorescence was carried out using Image J software on more than 30 yeasts on 3 different fields for each condition. The results were analyzed using the Student t test in which significance is attained at P <0.05.

Results

*Haliclona mucosa* Methanolic Fraction Contains Inhibitors of the Resistance of Patched-Expressing Yeasts to Doxorubicin.

Inventors cultured yeast S. *cerevisiae* expressing human Patched in their plasma membrane as previously described (Bidet et al., 2011, 2012) in 96 well plates. Methanolic fraction of *Haliclona mucosa* crude extracts was prepared, dissolved in DMSO at 10mg/mL and added at a final concentration of 10 µg/mL to the yeast culture medium supplemented or not with doxorubicin (dxr). As previously reported (Bidet et al., 2012), human Patched confers a resistance to growth inhibition by dxr, an alkylating agent used to treat a wide range of cancers (FIG. 2B). Methanolic fraction from *Haliclona mucosa* significantly inhibits the growth of hPtc-expressing yeast in presence of dxr with low effect on yeast growth by itself (in absence of dxr) (FIG. 2B). This suggests that methanolic fraction from *Haliclona mucosa* contains compounds able to inhibit the resistance to dxr of yeast over-expressing Patched.

The methanolic fraction from *Haliclona mucosa* was then purified by HPLC on preparative C18 reversed phase to yield 9 compounds (P1 to P9) (FIG. 2C). Purified fractions were added to the yeast growth medium in presence or absence of dxr (FIG. 2D). Five of these fractions were able to strongly inhibit the resistance of Patched-expressing yeasts to dxr: P2, P3, P5, P6 and P7. The effect of P4 and P9 on yeast growth was lighter.

The 1H NMR spectra allowed the identification of four of these compounds and confirmed their purity. These compounds are members of the panicein family: Panicein-C (P2), Panicein-B3 (P3), Panicein-B2 (P4) and Panicein-A-hydroquinone (P5) (FIG. 3).

Paniceins Purified from *Haliclona mucosa* Increase the Cytotoxicity of Doxorubicin for Melanoma Cells.

Three melanoma cell lines have been chosen to evaluate the effect of paniceins purified from *Haliclona mucosa* extract on the dxr cytotoxicity. MDA-MB-435 cells are derived from the M14 melanoma cell line and used to study cancer metastasis (Rae et al., 2007). MeWo cell line derived from melanoma metastatic site (lymph node tissue) and A375 cell line derived from a human malignant melanoma and carries the BRAF V600E mutation. These three cell lines over express the Patched protein as shown by western-blotting (FIG. 4A) and immunofluorescent labeling using Patched antibodies (FIG. 4B), and are known to have metastatic potential.

Cells were treated with paniceins and with or without dxr during 24 hours before cell viability measurement (FIG. 5). Results show that compounds P2, P3 and P4 increase by about 2 times the cell mortality induced by dxr on MDA-MB-435 and MeWo, but have no effect on A375. P5 increases by about 5 to 8 times the dxr cytotoxicity for MDA-MB-435 and MeWo, and 2 times the dxr cytotoxicity for A375. P5 induces 50% of dxr cytotoxicity enhancement at 9.3 µM, 5 µM and 22.5 µM for MDA-MB-435, MeWo and A375 cells respectively. Annexin V and DAPI labeling indicate that compound P5 increases early apoptosis (FIG. 10).

Western blot analysis performed on MEWO or A375 cells treated during 24 hours with panicein A hydroquinone or with DMSO indicated panicein A hydroquinone had no effect on Patched expression or degradation in these cells (FIG. 11).

Paniceins Inhibits Doxorubicin Efflux.

Melanoma cells grown on cover-slips were loaded with dxr, fixed (for loading control) or incubated with efflux buffer containing DMSO (efflux control) or paniceins, fixed and analyzed using cell imaging (FIGS. 6A and 12A). The dxr fluorescence intensity in cells was quantified for at least 30 cells by experiment and shows that the presence of compound P5 significantly increased (by about 25%) dxr into A375 and MeWo cells contrary to "healthy" keratinocytes HaCaT. These results suggest that Panicein A hydroquinone inhibits doxorubicin efflux from melanoma cells.

In order to see if Paniceins inhibit dxr efflux through Patched inhibition, inventors compared dxr efflux on yeasts over-expressing human Patched and control yeasts. After loading with dxr, yeasts were centrifuged and fixed for dxr loading control (LC), or resuspended in buffer supplemented with DMSO or paniceins for efflux measurements. After 10 min a 20° C., yeasts were collected, fixed and deposited on cover-slips. 2-deoxy-D-glucose was added in buffer during loading and efflux in order to inhibit ATP-binding cassette (ABC) transporters. Dxr fluorescence intensity of at least 30 yeasts was measured for each experiment. FIGS. 6A and 12A show the mean fluorescence intensity of 3 independent experiments. Dxr fluorescence measured in hPtc-expressing yeasts after efflux in control buffer (containing DMSO) was significantly lower than that measured in control yeasts according to the dxr efflux activity of Patched (Bidet et al., 2012). hPtc-expressing yeasts incubated with compounds P4 and P5 during efflux showed significantly higher amounts of dxr fluorescence contrary to control yeasts (FIGS. 6B and 12B and Table 2), suggesting that these compounds are able to inhibit significantly dxr efflux activity of Patched. This was confirmed using yeasts over-expressing Patched mutant VXXXY. Patched possesses a motif GXXXD in its putative fourth transmembrane segment which is highly conserved in Niemann-Pick disease protein (NPC1), and many bacterial MDR transporters of the RND family such as AcrB (Bidet et al., 2012). hPtcVXXXY carries the double mutation in which the glycine in position 509 was replaced by a valine and the aspartic acid in position 513 by a tyrosine. Yeasts over-expressing hPtcVXXXY are less resistance to growth inhibition by dxr than yeasts over-expressing wild-type hPtc (Bidet et al., 2012). According to previous observations, yeasts expressing the mutant protein hPtcVXXXY contained significantly more dxr after efflux than yeasts expressing wild-type hPtc (FIG. 6B). The amount of dxr in hPtcVXXXY yeasts is comparable to that in control yeasts confirming that hPtc transports dxr out of the cell. The presence of paniceins in the efflux buffer did not increase the dxr content in yeasts expressing hPtcVXXXY contrary to yeasts expressing wild-type hPtc (FIGS. 6B and 12B, Table 2). These results support the hypothesis that paniceins inhibit the dxr efflux activity of Patched.

TABLE 2

Inhibition of dxr efflux activity of Patched by paniceins

| | Efflux (%) | | | | |
|---|---|---|---|---|---|
| | DMSO | Panicein P2 | Panicein P3 | Panicein P4 | Panicein P5 |
| WT-hPtc-yeasts | 65 | 51 | 46 | 46 | 40 |
| hPtc-YXXXG-yeasts | 30 | 39 | 32 | 38 | 42 |
| Control-yeasts | 25 | 20 | 25 | 29 | 39 |

Panicein a Hydroquinone Presents a Strong Docking Cluster Close to the Doxorubin Binding Site in Both AcrB Structure and Patched Structural Model.

The crystal structure of AcrB, the principal multidrug efflux transporter from the RND family in *Escherichia coli*, was described with and without doxorubicin by Murakami et al. (2006). The AcrB-drug complex consists of three protomers, each of which has a different conformation corresponding to one of the three functional states of the transport cycle. Bound substrate was found in the periplasmic domain of one of the three protomers. The voluminous binding pocket is aromatic and allows multi-site binding.

Isabelle Broutin (Laboratoire de Cristallographie et RMN Biologiques, UMR 8015 CNRS, Faculte de Pharmacie Paris V France) carried out the docking of compounds P2 and P5 into the AcrB-dxr structure. The analysis shows many clusters of low probability for P2 binding, and more interestingly, a strong probability of binding of P5 in a cluster close to the dxr binding site. Isabelle Broutin then realized a model of the structure of Patched from the AcrB structure and carried out the docking with compounds P2 and P5 with the same results as those reported for the docking on AcrB structure (FIG. 7).

This analysis shows that panicein A hydroquinone could bind close to the dxr-binding site of Patched and prevent dxr binding. This is in good agreement with the inhibition of dxr efflux observed in presence of panicein A hydroquinone.

Paniceins also Inhibit Resistance to Dacarbazine and Cisplatine Conferred to Yeasts by Patched Over-expression.

The expression of human Patched in yeasts confers to these yeasts the ability to grow in presence of other chemotherapeutic agents currently used to treat melanoma such as dacarbazine or cisplatine. Inventors' results demonstrate that the presence of compounds P2, P3 or P5 in the growth medium inhibits the resistance of yeasts to dacarbazine, cisplatine and vemurafenib (FIG. 8).

Conclusion

Inventors' results show for the first time that some paniceins purified from the Mediterranean sponge *Haliclona mucosa*, in particular panicein A hydroquinone, are able to enhance doxorubicin cytotoxicity for melanoma cells in vitro. Efflux measurements strongly suggest that paniceins inhibit the dxr efflux activity of Patched. This hypothesis is supported by the docking realized on the structure of the *E. coli* multidrug transporter AcrB and on the structural model of Patched which shows that panicein A hydroquinone has a strong probability of binding close to the dxr binding site. This demonstrates that binding of panicein A hydroquinone to Patched prevents dxr efflux. These results also show that paniceins are able to inhibit the resistance conferred by Patched to other chemotherapeutic agents currently used to treat melanoma such as dacarbazine, cisplatine and vemurafenib.

REFERENCES

Becher O J, Hambardzumyan D, Fomchenko E I, Momota H, Mainwaring L, Bleau A M, Katz A M, Edgar M, Kenney A M, Cordon-Cardo C, et al. (2008) Cancer Res. 68: 2241-2249.

Berman D M, Karhadkar S S, Hallahan A R, Pritchard J I, Eberhart C G, Watkins D N, Chen J K, Cooper M K, Taipale J, Olson J M, et al. (2002) Science 297: 1559-1561.

Bergman W., Feeney R. J., J. Org. Chem. 1951, 16, 981-987, Nucleosides of sponges.

Bidet M, Tomico A, Martin P, Guizouarn H, Mollat P and Mus-Veteau I. (2012) Mol Cancer Res. 10:1496-1508.

Blanchet-Cadeddu A, Hénon E., Dauchez M., Renault J-H., Monneaux F., Haudrechy A., Org. Biomol. Chem. 2011, 9, 3080-3104, The stimulating adventure of KRN 7000.

Blotta S, Jakubikova J, Calimeri T, Roccaro A M, Amodio N, Azab A K, Foresta U, Mitsiades C S, Rossi M, Todoerti K, Molica S, Morabito F, Neri A, Tagliaferri P, Tassone P, Anderson K C, Munshi N C (2012) Blood. 120:5002-13.

Casapullo et al., Journal of Natural Products, 1993, 56, 4, 527-533

Cea M, Cagnetta A, Cirmena G, Garuti A, Rocco I, Palermo C, Pierri I, Reverberi D, Nencioni A, Ballestrero A, Gobbi M, Carella A M, Patrone F. (2013) Tracking molecular relapse of chronic myeloid leukemia by measuring Hedgehog signaling status. Leuk Lymphoma. February; 54(2):342-52.

Chung M K[1], Kim H J, Lee Y S, Han M E, Yoon S, Baek S Y, Kim B S, Kim J B, Oh S O. (2010) Hedgehog signaling regulates proliferation of prostate cancer cells via stathminl Clin Exp Med. March; 10(1):51-7.

Cimino et al., Tetrahedron, 1973, vol. 29, 2565-2570.

Casapullo A., Scognamiglio G., Cimino G., Tetrahedron 1997, 38, 3643-3646, Mucosin: a new bicyclic eicosanoid from the Mediterranean sponge Reniera mucosa.

Chen Y J, Pornillos O, Lieu S, Ma C, Chen A P, Chang G. (2007) Proc Natl Acad Sci USA. 104(48): 18999-9004.

Cheng X, Chen H. (2014) Tumor heterogeneity and resistance to EGFR-targeted therapy in advanced nonsmall cell lung cancer: challenges and perspectives. Onco Targets Ther. September 23; 7:1689-704.

Cimino G., De Stefano S., Minale L, Tetrahedron 1973, 29, 2565-2570, Paniceins, unusual aromatic sesquiterpenoids linked to a quinol or quinone system from the marine sponge *Halichondria panicea*.

Cretnik M[1], Poje G, Musani V, Kruslin B, Ozretic P, Tomas D, Situm M, Levanat S. (2009) Involvement of p16 and PTCH in pathogenesis of melanoma and basal cell carcinoma. Int J Oncol. April; 34(4):1045-50.

Cuevas C., Francesh A, Nat. Prod. Rep. 2009, 26, 322-337, Development of Yondelis® (trabectedin, ET-743). A semisynthetic process solves the supply problem.

Garber K (2008) J. Natl. Cancer Inst. 100: 692-697.

Davis et al., Journal of Organic Chemistry, 2005, 70, 4414-4422.

Dewick, in Medicinal Natural Products: A Biosynthetic Approach, 2nd ed. (Eds: J. Wiley and Son), West Sussex, U K, 2002, p. 520.

Duan Z, Zhang J, Ye S, Shen J, Choy E, Cote G, Harmon D, Mankin H, Hua Y, Zhang Y, Gray N S, Hornicek F J. (2014) A-770041 reverses paclitaxel and doxorubicin resistance in osteosarcoma cells. BMC Cancer. September 19; 14:681.

Fan C W, Chen T, Shang Y N, Gu Y Z, Zhang S L, Lu R, OuYang S R, Zhou X, Li Y, Meng W T, Hu J K, Lu Y, Sun X F, Bu H, Zhou Z G, Mo X M. (2013) Cancer-initiating cells derived from human rectal adenocarcinoma tissues carry mesenchymal phenotypes and resist drug therapies. Cell Death Dis. October 3; 4:e828.

Fonseca N A, Gomes-da-Silva L C, Moura V, Simões S, Moreira J N. (2014) Simultaneous active intracellular delivery of doxorubicin and C6-ceramide shifts the additive/antagonistic drug interaction of non-encapsulated combination. J Control Release. October 10.

Gialmanidis I P, Bravou V, Amanetopoulou S G, Varakis J, Kourea H, Papadaki H. (2009) Overexpression of hedgehog pathway molecules and FOXM1 in non-small cell lung carcinomas. Lung Cancer. October; 66(1):64-74.

Gunasekera S. P., Gunasekera M, Longley R. E., Schulte G. K., J. Org. Chem. 1990, 55, 4912-4915, Discodermolide: a new bioactive polyhydroxylated lactone from the marine sponge Discodermia dissoluta.

Hall T M, Porter J A, Beachy P A, Leahy D J. (1995) Nature, 378(6553):212-6.

He C, Liu D, Lin W. (2014) Self-assembled nanoscale coordination polymers carrying siRNAs and cisplatin for effective treatment of resistant ovarian cancer. Biomaterials. October 11.

Hinterseher U, Wunderlich A, Roth S, Ramaswamy A, Bartsch D K, Hauptmann S, Greene B H, Fendrich V, Hoffmann S. (2014) Expression of hedgehog signalling pathway in anaplastic thyroid cancer. Endocrine. April; 45(3):439-47.

Hirata Y., Uemura D., Pure & Appl. Chem. 1986, 58, 701-710, Halicondrins-antitumor polyether macrolides from a marine sponge.

Isidor B, Bourdeaut F, Lafon D, Plessis G, Lacaze E, Kannengiesser C, Rossignol S, Pichon O, Briand A, Martin-Coignard D, Piccione M, David A, Delattre O, Jeanpierre C, Sevenet N, Le Caignec C. (2013) Wilms' tumor in patients with 9q22.3 microdeletion syndrome suggests a role for PTCH1 in nephroblastomas. Eur J Hum Genet. July; 21(7):784-7.

Jahnke H G, Poenick S, Maschke J, Kendler M, Simon J C, Robitzki A A. (2014) Direct chemosensitivity monitoring ex vivo on undissociated melanoma tumor tissue by impedance spectroscopy. Cancer Res. September 29.

Jeng K-S, Sheen I-S, Jeng W-J, Yu M-C, Hsiau H-I and Chang F-Y (2014) OncoTargets and Therapy, 7, 79-86.

Karhadkar S S, Bova G S, Abdallah N, Dhara S, Gardner D, Maitra A, Isaacs J T, Berman D M, Beachy P A. (2004) Nature, 431:707-12.

Kim T J, Lee J Y, Hwang T K, Kang C S, Choi Y J. (2011) Hedgehog signaling protein expression and its association with prognostic parameters in prostate cancer: a retrospective study from the view point of new 2010 anatomic stage/prognostic groups. J Surg Oncol. October; 104(5):472-9.

Kimura H, Ng J M, and Curran T (2008) Cancer Cell 13: 249-260.

Kolosenko I, Fryknäs M, Forsberg S, Johnsson P, Cheon H, Holvey-Bates E G, Edsbäcker E, Pellegrini P, Rassoolzadeh H, Brnjic S, Larsson R, Stark G R, Grandér D, Linder S, Tamm K P, De Milito A. (2014) Cell crowding induces interferon regulatory factor 9, which confers resistance to chemotherapeutic drugs. Int J Cancer. August 23.

Lee S J, Do I G, Lee J, Kim K M, Jang J, Sohn I, Kang W K. (2013) Gastric cancer (GC) patients with hedgehog pathway activation: PTCH1 and GLI2 as independent prognostic factors. Target Oncol. December; 8(4): 271-80.

Lehmann-Che J, Bally C, de Thé H. (2014) Resistance to therapy in acute promyelocytic leukemia. N Engl J Med. September 18; 371(12):1170-2.

Li Y, Zhang D, Chen C, Ruan Z, Li Y, Huang Y. (2012) MicroRNA-212 displays tumor-promoting properties in non-small cell lung cancer cells and targets the hedgehog pathway receptor PTCH1. Mol Biol Cell. April; 23(8):1423-34.

Lo W W, Wunder J S, Dickson B C, Campbell V, McGovern K, Alman B A, Andrulis I L. (2014) Involvement and targeted intervention of dysregulated Hedgehog signaling in osteosarcoma. Cancer. February 15; 120(4):537-47. 21.

Long F, Su C C, Zimmermann M T, Boyken S E, Rajashankar K R, Jernigan R L, Yu E W. (2010) Nature. 467:484-8.

Ma C, Nong K, Wu B, Dong B, Bai Y, Zhu H, Wang W, Huang X, Yuan Z, Ai K. (2014) miR-212 promotes pancreatic cancer cell growth and invasion by targeting the hedgehog signaling pathway receptor patched-1. J Exp Clin Cancer Res. June 25; 33:54.

Ma R, Minsky N, Morshed S A, Davies T F. (2014) Stemness in human thyroid cancers and derived cell lines: the role of asymmetrically dividing cancer stem cells resistant to chemotherapy. J Clin Endocrinol Metab. March; 99(3):E400-9.

Miljanich, Curr. Med. Chem. 2004, 11, 3029-3040, Zicotonide: Neural calcium channel blocker for treating severe chronic pain.

Murakami S, Nakashima R, Yamashita E, Matsumoto T, Yamaguchi A. (2006) Nature. 443:173-9. Crystal structures of a multidrug transporter reveal a functionally rotating mechanism.

Mus-Veteau, Bidet, Novel therapeutic strategies for improving an anticancer treatment, FR2011052927/WO2012080630, 13.12.2010, I.

Nagase T, Nagase M, Machida M and Fujita T (2008) Angiogenesis 11: 71-77.

Nakamura M, Kubo M, Yanai K, Mikami Y, Ikebe M, Nagai S, Yamaguchi K, Tanaka M, Katano M. (2007) Anticancer Res. 27(6A):3743-7.

Nakamura M, Tanaka H, Nagayoshi Y, Nakashima H, Tsutsumi K, Ohtsuka T, Takahata S, Tanaka M, Okada H. (2012) J Gastroenterol. 47:452-60.

Oue T, Yoneda A, Uehara S, Yamanaka H, Fukuzawa M. (2010) Increased expression of the hedgehog signaling pathway in pediatric solid malignancies. J Pediatr Surg. February; 45(2):387-92.

Parks L. (2014) New target for resistant prostate cancer. Ther Deliv. June; 5(6):617.

Pola R, Ling L E, Silver M, Corbley M J, Kearney M, Blake Pepinsky R, Shapiro R, Taylor F R, Baker D P, Asahara T, et al. (2001) Nat. Med. 7: 706-711.

Qualtrough D, Buda A, Gaffield W, Williams A C, Paraskeva C. (2004) Int J Cancer. Hedgehog signalling in colorectal tumour cells: induction of apoptosis with cyclopamine treatment. July 20; 110(6):831-7.

Queiroz K C, Ruela-de-Sousa R R, Fuhler G M, Aberson H L, Ferreira C V, Peppelenbosch M P, et al. (2010) Oncogene 29:6314-22.

Rae J M, Creighton C J, Meck J M, Haddad B R, Johnson M D.MDA-MB-435 cells are derived from M14 melanoma cells—a loss for breastcancer, but a boon for melanoma research. Breast Cancer Res Treat 2007; 104:13-9.

Sabol M, Car D, Musani V, Ozretic P, Oreskovic S, Weber I, Levanat S. (2012) The Hedgehog signaling pathway in ovarian teratoma is stimulated by Sonic Hedgehog which induces internalization of Patched. Int J Oncol. October; 41(4):1411-8.

Saze Z, Terashima M, Kogure M, Ohsuka F, Suzuki H, Gotoh M. (2012) Dig Surg. 29:115-23.

Scales S and de Sauvage F (2009) Trends Pharmacol Sci 30, 303-312.

Sennhauser G, Bukowska M A, Briand C, Grütter M G. (2009) J. Mol. Biol. 389:134-45.

Smith D, Kong F, Yang D, Larson R, Sims-Mourtada J, Woodward W A. (2014) Patched targeting peptides for imaging and treatment of hedgehog positive breast tumors. Biomed Res Int. 525680. doi: 10.1155/2014/525680. Epub 2014 Sep. 8.

Taipale J, Chen J K, Cooper M K, Wang B, Mann R K, Milenkovic L, Scott M P and Beachy P A (2000) Nature 406: 1005-1009.

Varjosalo M, Taipale J. (2008) Genes Dev., 22:2454-72.

Vinokthkumar S., Parameswaran P. S., Biotechnol. Adv. 2013, in press, Recent advances in marine drug research.

Xu M[1], Li X, Liu T, Leng A, Zhang G. (2012) Prognostic value of hedgehog signaling pathway in patients with colon cancer. Med Oncol. June; 29(2):1010-6.

Xu X, Ding H, Rao G, Arora S, Saclarides C P, Esparaz J, Gattuso P, Solorzano C C, Prinz R A (2012) Endocr Relat Cancer. 19:167-79.
Yu F Y, Hong Y Y, Qu J F, Chen F, Li T J. (2014) The large intracellular loop of ptch1 mediates the non-canonical Hedgehog pathway through cyclin B1 in nevoid basal cell carcinoma syndrome. Int J Mol Med. 2014 August; 34(2):507-12.
Yue D, Li H, Che J, Zhang Y, Tseng H H, Jin J Q, Luh T M, Giroux-Leprieur E, Mo M, Zheng Q, Shi H, Zhang H, Hao X, Wang C, Jablons D M, He B (2014) J Exp Clin Cancer Res. 33(1):34.
Watkins D N, Berman D M, Burkholder S G, Wang B, Beachy P A, and Baylin S B (2003) Nature 422: 313-317.
Wang C, Wu H, Katritch V, Han G W, Huang X-P, Liu W, Siu F Y, Roth B L, Cherezov V and Stevens R C (2013) Nature. 497:338-43.
Wang Z C, Gao J, Zi S M, Yang M, Du P, Cui L. (2013) Aberrant expression of sonic hedgehog pathway in colon cancer and melanosis *coli*. J Dig Dis. August; 14(8):417-24.
Woo S R, Ham Y, Kang W, Yang H, Kim S, Jin J, Joo K M, Nam D H. (2014) KML001, a Telomere-Targeting Drug, Sensitizes Glioblastoma Cells to Temozolomide Chemotherapy and Radiotherapy through DNA Damage and Apoptosis. Cancers résistants aux chimiothérapies: Biomed Res Int.; 2014:747415.
Wu H, Wang C, Gregory K J, Han G W, Cho H P, Xia Y, Niswender C M, Katritch V, Meiler J, Cherezov V, et al. (2014) Science. 344:58-64.
Zhao C, Chen A, Jamieson C H, Fereshteh M, Abrahamsson A, Blum J, et al. (2009) Nature. 458:776-9.
Zhou Y, Dai R, Mao L, Xia Y, Yao Y, Yang X, Hu B. (2010) Activation of Sonic hedgehog signaling pathway in S-type neuroblastoma cell lines. J Huazhong Univ Sci Technolog Med Sci. June; 30(3):271-7.
Zhu W, You Z, Li T, Yu C, Tao G, Hu M, Chen X. (2011) Correlation of hedgehog signal activation with chemoradiotherapy sensitivity and survival in esophageal squamous cell carcinomas. Jpn J Clin Oncol. March; 41(3):386-93.
Zhu W, Li J, Wu S, Li S, Le L, Su X, Qiu P, Hu H, Yan G. (2012) Triptolide cooperates with Cisplatin to induce apoptosis in gemcitabine-resistant pancreatic cancer. Pancreas. October; 41(7):1029-38.
Zubia E., Ortega M. J., Carballo J. L, Salva J., Tetrahedron 1994, 50, 8153-8160, Sesquiterpene hydroquinones from the sponge Reniera mucosa.

We claim:

1. A method for treating a cancer, for reducing cancer metastasis and/or cancer recurrence in a subject comprising a step of administering to a subject a panicein compound in combination with at least one chemotherapeutic drug, wherein the cancer comprises cancer cells expressing the Patched receptor, and wherein the panicein compound is of formula (I)

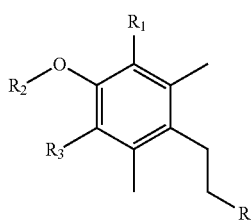

wherein:
$R_1$ is H, $C_1$-$C_6$ alkyl, $C_1$-$C_6$ aminoalkyl, $C_1$-$C_6$ hydroxyalkyl, $C_1$-$C_6$ halogenoalkyl or —$OR_4$,
$R_2$ is H or $C_1$-$C_6$ alkyl,
$R_3$ is $C_1$-$C_6$ alkyl, —$CH_2OR_4$, —C(=O)$R_4$, —C(=O)$OR_4$, —C(=O)$NHR_4$, or —$CH_2NHR_4$,
each $R_4$ is independently —H, or $C_1$-$C_6$ alkyl,
R is:

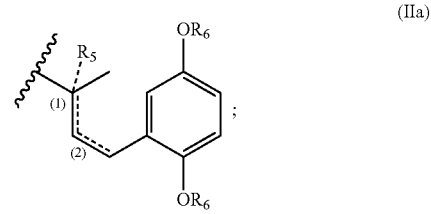

wherein:
bonds (1) and (2) are independently of each other a single bond or a double bond and bonds (1) and (2) are not simultaneously double bonds,
$R_5$ is present when bond (1) is a single bond, and represents —H, or —$OR_6$, and
when present, each $R_6$ is independently H or a $C_1$-$C_6$ alkyl; or a pharmaceutically acceptable salt thereof; and
wherein cancer is selected from a melanoma, a breast cancer, a thyroid cancer, a prostate cancer, an esophagus cancer, a gastric cancer, an ovarian cancer, a pancreatic cancer, a glioma, an adrenocortical carcinoma, a leukemia, a multiple myeloma or a sarcoma; and
wherein the at least one chemotherapeutic drug is selected from cisplatin, docetaxel, doxorubicin, methotrexate, temozolomide, 5-fluorouracil (5-FU), dacarbazine and vemurafenib.

2. The method according to claim 1, wherein, when present, R is selected from the group consisting of:

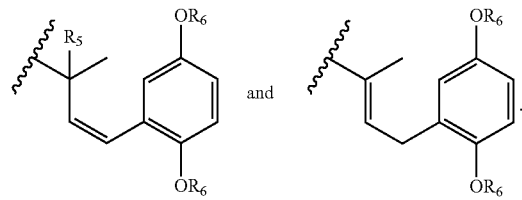

3. The method according to claim 1, wherein the compound of formula (I) comprises the following features:
i) $R_1$ is H, $C_1$-$C_6$ alkyl or —$OR_4$,
ii) $R_2$ is H or $C_1$-$C_6$ alkyl,
iii) $R_3$ is $C_1$-$C_6$ alkyl, —$CH_2OR_4$ or —C(=O)$R_4$, and
iv) when present, each $R_4$ is independently —H, or a $C_1$-$C_6$ alkyl or a $C_1$-$C_3$ alkyl.

4. The method according to claim 1, wherein the compound of formula (I) is selected from Panicein C, Panicein B3 and Panicein A hydroquinone.

5. The method according to claim 4, wherein the compound of formula (I) is Panicein A hydroquinone.

6. The method according to claim 1, wherein the panicein compound decreases or inhibits the Patched receptor drug efflux activity.

7. The method according to claim 2, wherein $R_6$ is H and $R_5$ is H or OH.

8. The method according to claim 1, wherein the subject is a mammal.

9. The method according to claim 8, wherein the subject is a human being suffering of a cancer and resistant to chemotherapy.

10. The method according to claim 1, wherein it increases the sensitivity of the cancer to the at least one chemotherapeutic drug.

11. The method according to claim 1, wherein it decreases the resistance of the cancer with respect to the at least one chemotherapeutic drug.

12. The method according to claim 1, wherein the cancer is selected from a melanoma, a breast cancer, an adrenocortical carcinoma and a leukemia, and wherein the chemotherapeutic drug is selected from cisplatin, docetaxel, doxorubicin, dacarbazine and vemurafenib.

13. A method for treating cancer, for reducing cancer metastasis and/or cancer recurrence in a subject comprising a step of administering panicein A hydroquinone in combination with at least one chemotherapeutic drug to the subject, wherein the cancer is selected from a melanoma, a breast cancer, a thyroid cancer, a prostate cancer, an esophagus cancer, a gastric cancer, an ovarian cancer, a pancreatic cancer, a glioma, an adrenocortical carcinoma, a leukemia, a multiple myeloma or a sarcoma; and wherein the at least one chemotherapeutic drug is selected from cisplatin, docetaxel, doxorubicin, methotrexate, temozolomide, 5-FU, dacarbazine and vemurafenib.

14. The method according to claim 13, wherein the cancer is melanoma and the chemotherapeutic drug is vemurafenib.

\* \* \* \* \*